US009895338B1

(12) United States Patent
Wong et al.

(10) Patent No.: US 9,895,338 B1
(45) Date of Patent: Feb. 20, 2018

(54) COBALT-POLYPYRIDYL COMPLEX FOR TREATMENT OF CANCER, A PHARMACEUTICAL COMPOSITION AND A KIT COMPRISING IT

(71) Applicant: Macau University of Science and Technology, Taipa (MO)

(72) Inventors: Kam Wai Wong, Taipa (MO); Man Chung Wong, Taipa (MO)

(73) Assignee: Macau University of Science and Technology, Taipa (MO)

( * ) Notice: Subject to any disclaimer, the term of this patent is extended or adjusted under 35 U.S.C. 154(b) by 0 days.

(21) Appl. No.: 15/242,883

(22) Filed: Aug. 22, 2016

(51) Int. Cl.
*A61K 31/28* (2006.01)
*A61K 31/555* (2006.01)
*A61K 45/06* (2006.01)

(52) U.S. Cl.
CPC ............ *A61K 31/28* (2013.01); *A61K 31/555* (2013.01); *A61K 45/06* (2013.01)

(58) Field of Classification Search
CPC ...................................... A61K 31/28
USPC ........................................ 514/188
See application file for complete search history.

(56) References Cited

PUBLICATIONS

Feldt et al, Journal of American Chemical Society (2010), vol. 132, pp. 16714-16724.*

M. Frezza, S. Hindo, D. Chen, A. Davenport, S. Schmitt, D. Tomco, and Q. P. Dou, "Novel Metals and Metal Complexes as Platforms for Cancer Therapy", Current Pharmaceutical Design, 2010, 16, pp. 1813-1825.

S. Dasari and P. B. Tchounwou, "Cisplatin in cancer therapy: Molecular mechanisms of action", Eur J Pharmacol (2014), http://dx.doi.org/10.1016/j.ejphar.2014.07.025.

I. Ott, "On the medicinal chemistry of gold complexes as anticancer drugs", Coordination Chemistry Reviews 253 (2009) pp. 1670-1681.

S. Nobili, E. Mini, I. Landini, C. Gabbiani, A. Casini, and L. Messori, "Gold Compounds as Anticancer Agents: Chemistry, Cellular Pharmacology, and Preclinical Studies", Medicinal Research Reviews, vol. 30, No. 3, pp. 550-580, 2010.

I. Romero-Canelon and P. J. Sadler, "Next-Generation Metal Anticancer Complexes: Multitargeting via Redox Modulation", Inorganic Chemistry, 2013, 52, pp. 12276-12291.

(Continued)

*Primary Examiner* — Kathrien Cruz
*Assistant Examiner* — Janet L Coppins
(74) *Attorney, Agent, or Firm* — Renner, Kenner, Greive, Bobak, Taylor & Webr Co., LPA

(57) ABSTRACT

A method for treating a subject suffering from a cancer, in particular a multidrug-resistant cancer includes administrating a cobalt-polypyridyl complex to the subject. A method for suppressing the growth of cancer cells, in particular inducing autophagy of the cancer cells, inducing cell cycle arrest of the cancer cells and/or inhibiting cell invasion of the cancer cells and for specifically targeting cancer cells with multidrug-resistance includes contacting said cancer cells with the cobalt-polypyridyl complex. A pharmaceutical composition and a kit are provided and include the cobalt-polypyridyl complex. Unexpectedly, the cobalt-polypyridyl complex is especially suitable to treat cancer, in particular multidrug-resistant cancer with an exceptionally increased cytotoxic activity towards multidrug-resistant cancer cells.

17 Claims, 8 Drawing Sheets
(2 of 8 Drawing Sheet(s) Filed in Color)

(56) References Cited

PUBLICATIONS

K. Suntharalingam, W. Lin, T. C. Johnstone, P. M. Bruno, Y-R. Zheng, M. T. Hemann, and S. J. Lippard, "A Breast Cancer Stem Cell-Selective, Mammospheres-Potent Osmium(VI) Nitrido Complex", J. Amer. Chem. Soc., 2014, 136, pp. 14413-14416.

T. Zou, C. T. Lum, C-N. Lok, J-J. Zhang, and C-M. Che, "Chemical biology of anticancer gold(III) and gold(I) complexes", Chem Soc Rev, 2015, 44, pp. 8786-8801.

A. A. Jensen and F. Tuchsen, "Cobalt Exposure and Cancer Rise", Crit Rev Toxicol, 1990, 20, pp. 427-439.

M. C. Heffern, N. Yamamoto, R. J. Holbrook, A. L. Eckermann, and T. J. Meade, "Current Opinion in Chemical Biology", 2013, 17, pp. 189-196.

T. Takeuchi, A. Bottcher, C. M. Quezada, M. I. Simon, T. J. Meade, and H. B. Gray, "Selective Inihibition of Human a-Thrombin by Cobalt(III) Schiff Base Complexes", J. Amer. Chem. Soc. 1998, 120, pp. 8555-8556.

A. S. Harney, J. Lee, L. M. Manus, P. Wang, D. M. Ballweg, C. Labonne, and T. J. Meade, "Targeted inhibition of Snail family zinc finger transcription factors by oligonucleotide-Co(III) Schiff base conjugate", PNAS, 2009, vol. 106, No. 33, pp. 13667-13672.

M. D. Peterson, R. J. Holbrook, T. J. Meade, and E. A. Weiss, "Photoinduced Electron Transfer from PbS Quantum Dots to Cobalt(III) Schiff Base Complexes: Light Activation of a Protein Inhibitor", J. Amer. Chem. Soc., 2013, 135, pp. 13162-13167.

D. Luis, J. Silva, A. Tomaz, R. De Almeida, M. Larguinho, P. Baptista, L. Martins, T. Silva, P. Borralho, C. Rodrigues, A. Rodrigues, A. Pombeiro and A. Fernandes, "Insights into the mechanisms underlying the antiproliferative potential of a Co(II) coordination compound bearing 1,10-phenanthroline-5,6-dione: DNA and protein interaction studies", J. Biol. Inorg. Chem. (2014) 19, pp. 787-803.

G. Vignesh, R. Senthilkumar, P. Paul, V. S. Periasamy, M. A. Akbarsha, and S. Arunachalam, "Protein binding and biological evaluation of a polymer-anchored cobalt(III) complex containing a 2,2'-bipyridine ligand", RSC Adv., 2014, 4, pp. 57483-57492.

S. M. Feldt, E. A. Gibson, E. Gabrielsson, L. Sun, G. Boschloo, and A. Hagfeldt, "Design of Organic Dyes and Cobalt Polypyridine Redox Mediators for High-Efficiency Dye-Sensitized Solar Cells", J. Amer. Chem. Soc. 2010, 132, pp. 16714-16724.

B. M. Klahr and T. W. Hamann, Performance Enhancement and Limitations of Cobalt Bipyridyl Redox Shuttles in Dye-Sensitized Solar Cells, J. Phys. Chem. C 2009, 113, pp. 14040-14045.

Y. Xie and T. W. Hamann, "Fast Low-Spin Cobalt Complex Redox Shuttles for Dye-Sensitized Solar Cells", J. Phys. Chem. Lett., 2013, 4, pp. 328-332.

H-S. Kim, S-B. Ko, I-H. Jang, and N-G. Park, "Improvement of mass transport of the [Co(byp)3]II/III redox couple by controlling nanostructure of TiO2 films in dye-sensitized solar cells", Chem. Commun, 2011, 47, pp. 12637-12639.

Z. Sun, M. Liang, and J. Chen, "Kinetics of Iodine-Free Redox Shuttles in Dye-Sensitized Solar Cells: Interfacial Recombination and Dye Regeneration", Acc. Chem. Res., 2015, 48, pp. 1541-1550.

V. Wong, T. Li, B. Law, E. Ma, N. Yip, F. Michelangeli, C. Law, M. Zhang, K. Lam, P. Chan, and L. Liu, "Saikosaponin-d, a novel SERCA inhibitor, induces autophagic cell death in apoptosis-defective cells", Cell Death and Disease (2013) 4, e720; doi: 10.1038/cddis.2013.217.

V. Wong, H. Dong, X. Liang, L-P. Bai, Z-H. Jiang, Y. Guo, A-N. Kong, R. Wang, R. Kam, B. Law, W. Hsiao, K. Chan, J. Wang, R. Chan, J. Guo, W. Zhang, F. Yen, H. Zhou, E. Leung, Z. Yu and L. Liu, Rh2E2, a novel metabolic suppressor, specifically inhibits energy-based metabolism of tumor cells, Oncotarget, vol. 7, No. 9, pp. 9907-9924.

\* cited by examiner

COBALT-POLYPYRIDYL COMPLEX FOR TREATMENT OF CANCER, A PHARMACEUTICAL COMPOSITION AND A KIT COMPRISING IT

TECHNICAL FIELD

The present invention relates in a first aspect to a method for treating a subject suffering from a cancer, in particular a multidrug-resistant cancer, i.e. a cancer with multidrug-resistant phenotype and, thus, a specific subgroup of subjects with cancer. The method comprises administrating a cobalt-polypyridyl complex to said subject. In another aspect of the present invention, a method for suppressing the growth of cancer cells, in particular inducing autophagy of the cancer cells, inducing cell cycle arrest of the cancer cells and/or inhibiting cell invasion of the cancer cells and for specifically targeting cancer cells with multidrug-resistance is provided comprising contacting said cancer cells with the cobalt-polypyridyl complex. In a further aspect, the present invention provides a pharmaceutical composition and a kit comprising the cobalt-polypyridyl complex.

BACKGROUND OF THE INVENTION

Cancer is still a life-threatening disease affecting an increasing number of people in the world. Platinating compounds including cisplatin, carboplatin, and oxaliplatin are common chemotherapeutic compounds used for treating cancer. However, a significant number of patients have acquired or develop resistance to these chemotherapeutic compounds after initial therapeutic treatments. Such drug-resistance in cancer is the major impediment to a successful treatment. Such cells display a reduced sensitivity to chemotherapeutic compounds based on several mechanisms in particular including an increase in drug efflux such as by an increased expression or activity of ABC transporter proteins such as P-glycoprotein (P-gp, MDR1, or ABCB1) or affected apoptosis pathways such as by mutated or dysfunctionally regulated genes and respective proteins. For example, cancer cells lacking cell death mediators Bax and Bak have been reported to develop drug-resistance and the high frequency of p53 mutations is expected to lead to a drug resistance of cancer cells, too.

Therefore, different approaches have been applied to identify novel therapeutic agents, molecular mechanisms and targets for treating cancer which are also suitable to overcome drug resistance.

Transition metal ions are essential for the proper functions of organisms; examples including copper, iron, and manganese ions work with proteins and enzymes for multiple biological processes such as electron transfer and catalysis. As metals are involved in redox activity, coordination, and reactivity towards organic substrates in organisms, and are tightly regulated under normal conditions, aberrant metal ion concentrations are associated with pathogenesis of diseases, in particular of cancers. For instance, enriched copper ions found in cancer tissues are suggested to promote the angiogenesis processes in tumors.

In fact, metal-containing compounds have been used to treat a wide range of diseases. For example, cisplatin (cis-[PtII(NH$_3$)$_2$Cl$_2$]) can bind to the purine bases of the DNA, thereby led to DNA damage resulting in apoptosis in cancer cells. However, due to severe side effects such as dose-dependent toxicity, allergy, effects on the kidneys and immunity, gastrointestinal disorders, hemorrhage and loss of hearing, the clinical use of cisplatin is limited. Acquired resistance to cisplatin is caused by an increased efflux or detoxification of the drug, increased rate of DNA repair, as well as a reduced susceptibility of cancer cells in response to drug-induced cell death. Other platinum-containing anti-cancer analogs such as carboplatin and oxaliplatin are therefore used as alternative to cisplatin and further transition metal complexes including zinc(II), copper(II), gold(III), copper chelating agents, and non-platinum metal complexes such as ruthenium-containing compounds were studied for their potential as anti-cancer agents, too.

The exploration and exploitation of other non-platinum anti-cancer drugs have received considerable attention. In view of the fact that soluble cobalt salts can adversely interfere with cell division and bind to nucleic acids inside the cell nucleus, one may postulate that cobalt complexes could work as anti-cancer agents like platinum-containing analogs. However, they were also reported for being weakly mutagenic and inducing metastasis in animal models (Jensen A. A. and Tuchsen F., Crit Rev Toxicol, 1990, 20, 427-437). There have been some examples of cobalt(III) complexes with equatorial tetradentate Schiff base ligands as potent inhibitors of a wide range of zinc-dependent proteins (Heffern, M. C. et al., Curr Opin Chem Biol, 2013, 17, 189-196, Takeuchi, T. et al., J. Am. Chem. Soc., 1998, 120, 8555-8556, Harney, A. S. et al., Proc Natl Acad Sci USA, 2009, 106, 13667-13672, Peterson, M. D, J Am Chem Soc, 2013, 135, 13162-13167), however, the related use of cobalt pyridine complexes in biological applications or specifically for the development of anti-cancer drugs remains substantially unexplored (Luis, D. V. et al., J Biol Inorg Chem, 2014, 19, 787-803, Vignesh, G. et al., Rsc Advances, 2014, 4, 57483-57492). On the other hand, cobalt(II)/(III) complexes with pyridine ligands have recently been developed as redox mediators in dye-sensitized solar cells (DSCs) (Feldt, S. M., et al., J Am Chem Soc, 2010, 132, 16714-16724, Klahr, B. M. and Hamann, T. W., J Phys Chem C, 2009, 113, 14040-14045, Xie, Y. and Hamann, T. W., J Phys Chem Lett, 2013, 4, 328-332, Kim, H. S. et al., Chem Commun (Camb), 2011, 47, 12637-12639, Sun, Z. et al., Acc Chem Res, 2015, 48, 1541-1550), but not in the field of cancer treatment or the specific treatment of multidrug-resistant cancer.

Although there has been increased research in this regard, there remains a strong need for methods and means allowing for an effective therapeutic treatment of cancer, especially of multidrug-resistant cancer and cancer cells with a multidrug-resistant phenotype, respectively. In particular, efficacious treatment options are urgently required for specifically treating subjects with cancer such as with overexpression of ABC transporter proteins and/or decreased expression of pro-apoptotic proteins, i.e. for treating said specific subgroups of subjects with multidrug-resistant cancer among subjects with cancer.

SUMMARY OF THE INVENTION

The present invention relates in a first aspect to a method for treating a subject suffering from cancer, in particular multidrug-resistant cancer, i.e. a cancer with multidrug-resistant phenotype such as ABC-protein-dependent, in particular at least P-glycoprotein-dependent cancer, and/or cancer being apoptosis-deficient, in particular being at least p53-deficient. Said method of treating the subject with cancer, in particular with multidrug-resistant cancer, comprises the step of administering an effective amount of a cobalt-polypyridyl complex to said subject.

The cobalt-polypyridyl complex administered according to the present invention comprises a cobalt ion and at least one polypyridyl ligand of Formula (I):

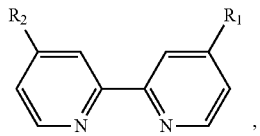

Formula (I)

wherein $R_1$ and $R_2$ are independently selected from hydrogen, a $C_1$-$C_{10}$ alkyl or a $C_1$-$C_{10}$ alkoxy. In particular, $R_1$ and $R_2$ are identical. In particular embodiments of the present invention, $R_1$ and $R_2$ are identical and selected from —H, —CH$_3$, —C$_9$H$_{19}$ or —OCH$_3$.

In particular, the cobalt-polypyridyl complex of the present invention comprises a structure of Formula (II):

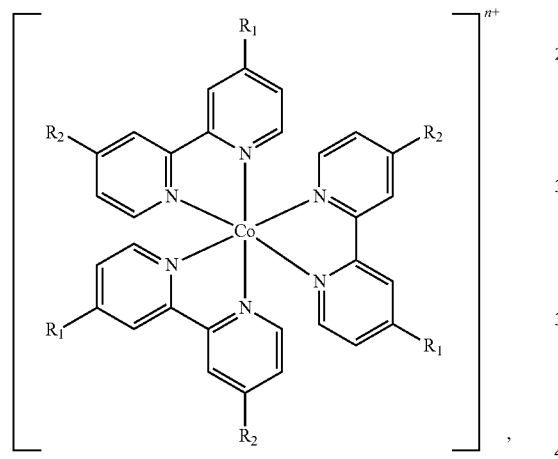

Formula (II)

wherein $R_1$ and $R_2$ are identical and selected from —H, —CH$_3$, —C$_9$H$_{19}$ or —OCH$_3$ and wherein n is 2 or 3, i.e. the cobalt-polypyridyl complex comprises a structure of one of Formula (III), (IV), (V), (VI), (VII) or (VIII):

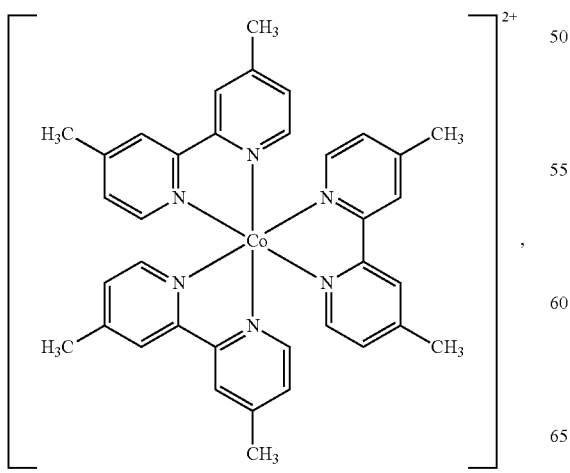

Formula (III)

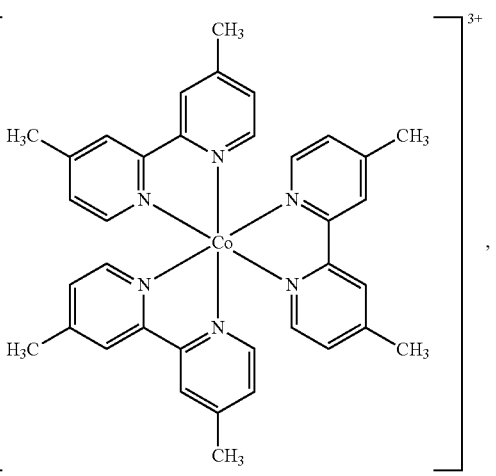

Formula (IV)

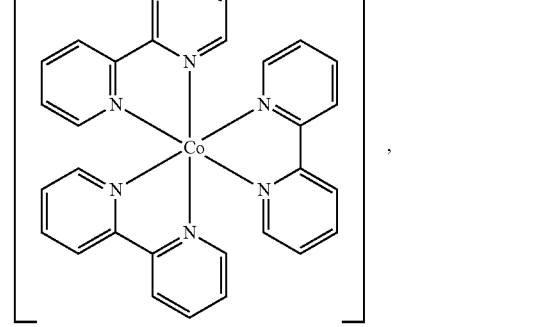

Formula (V)

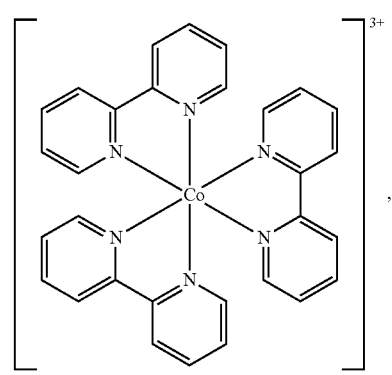

Formula (VI)

-continued

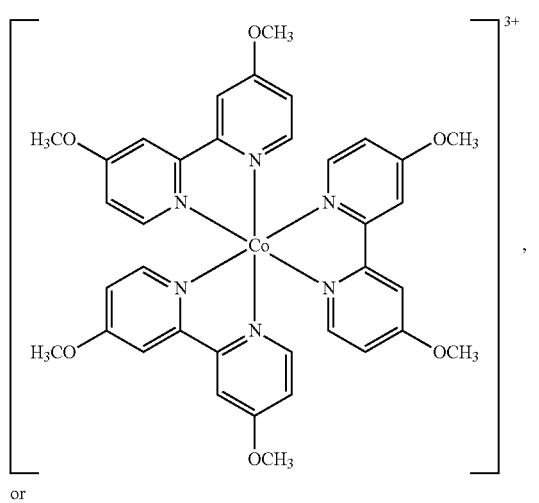

Formula (VII)

or

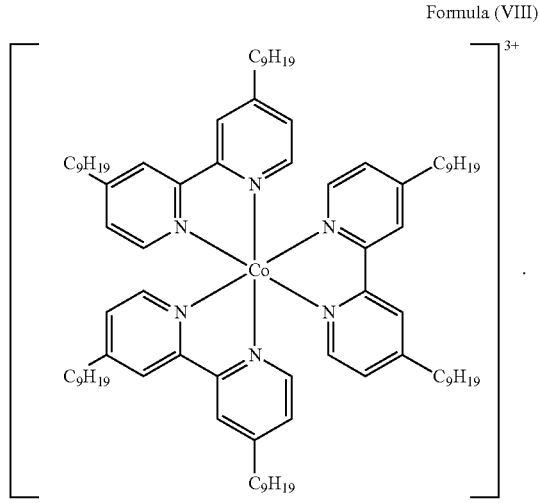

Formula (VIII)

The cobalt-polypyridyl complex of the present invention may further comprise a counterion in particular selected from, but not limited to, a monovalent anion such as hexafluorophosphate ($PF_6^-$) or chloride ($Cl^-$).

The cobalt-polypyridyl complex of the present invention may be administered in combination with at least one further chemotherapeutic compound, in particular selected from the group consisting of a topoisomerase-II inhibitor, an anthracycline, a coordination complex of platinum, a taxane, a protein kinase inhibitor, a *vinca* alkaloid or derivative thereof, a topoisomerase-I inhibitor and a nucleotide analog or precursor analog. Alternatively or additionally, the cobalt-polypyridyl complex of the present invention may be administered in combination with radiotherapy and/or immunotherapy.

According to the invention is also the cobalt-polypyridyl complex described above for use as a medicament for the treatment of cancer, in particular multidrug-resistant cancer such as P-glycoprotein-dependent multidrug-resistant cancer or p53-deficient multidrug-resistant cancer. Another aspect of the invention refers to the use of the cobalt-polypyridyl complex described above for preparing a medicament for treatment of cancer, in particular multidrug-resistant cancer such as P-glycoprotein-dependent or p53-deficient multidrug-resistant cancer. The present invention also relates to the use of the cobalt-polypyridyl complex as described above for suppressing cancer growth, in particular for inducing autophagy, inducing cell cycle arrest and/or inhibiting cell invasion.

The present invention further provides a method for suppressing the growth of cancer cells comprising contacting the cancer cells with an effective amount of a cobalt-polypyridyl complex, wherein the cobalt-polypyridyl complex comprises a cobalt ion and at least one polypyridyl ligand of Formula (I):

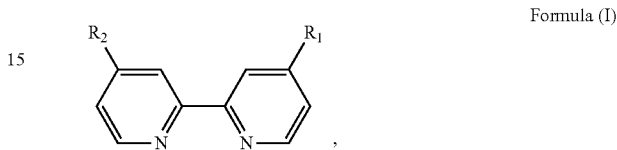

Formula (I)

wherein $R_1$ and $R_2$ are independently selected from hydrogen, a $C_1$-$C_{10}$ alkyl or a $C_1$-$C_{10}$ alkoxy. Preferably, the method is for inducing autophagy of the cancer cells, inducing cell cycle arrest of the cancer cells and/or inhibiting cell invasion of the cancer cells. The cancer cells are preferably multidrug-resistant cancer cells and more preferably at least one of (i) multidrug-resistant ABC-protein-dependent, in particular P-glycoprotein-dependent, multidrug-resistant cancer cells and/or (ii) apoptosis-deficient multidrug-resistant cancer cells, in particular p53-deficient multidrug-resistant cancer cells. The multidrug-resistant cancer cells are preferably at least resistant against taxol.

In another aspect of the present invention, a method for specifically targeting cancer cells with multidrug-resistance is provided, in particular ABC-protein-dependent such as P-glycoprotein-dependent or apoptosis-deficient such as p53-deficient multidrug-resistant cancer cells. Said method comprises the step of contacting a population of cancer cells with multidrug-resistance with a cobalt-polypyridyl complex as described above. In particular, the growth of the multidrug-resistant cancer cells is suppressed, preferably autophagy of the multidrug-resistant cancer cells is induced, cell cycle arrest of the multidrug-resistant cancer cells is induced and/or cell invasion of the multidrug-resistant cancer cells is inhibited.

Further in accordance with the present invention is a composition comprising the cobalt-polypyridyl complex and an excipient such as selected from a pharmaceutically acceptable carrier, salt, buffer, water, or a combination thereof. More preferably, the composition is a pharmaceutical composition comprising the cobalt-polypyridyl complex described above and at least one pharmaceutically acceptable excipient such as selected from a diluent, a filler, a binder, a disintegrant, a lubricant, a coloring agent, a surfactant or a preservative.

The present invention also provides a kit comprising an effective dose of the cobalt-polypyridyl complex as described above and an effective dose of at least a further chemotherapeutic compound commonly used for treating cancer, namely selected from the group consisting of a topoisomerase-II inhibitor, an anthracycline, a coordination complex of platinum, a taxane, a protein kinase inhibitor, a *vinca* alkaloid or derivative thereof, a topoisomerase-I inhibitor and a nucleotide analog or precursor analog. The kit may further comprise excipients, in particular pharmaceutically acceptable excipients, such as a carrier, salt, buffer, water, or a combination thereof. Accordingly, the present invention provides a novel and highly advantageous treatment option for treating cancer from various origins. It has been found that the cobalt-polypyridyl complex as described above, in particular a cobalt-polypyridyl complex comprising a structure of Formula (III), (IV) or (VII) is especially suitable for treating cancer and especially multidrug-resistant cancer as it possesses a high cytotoxic activity against cancer cells and specifically towards multidrug-resistant cancer cells such as of human origin. Said cobalt-polypyridyl complex described above, thus, allows for effectively targeting cancer and especially multidrug-resistant cancer, either alone or in combination with conventional chemotherapeutic compounds. It provides an advantageous treatment approach for cancer exceptionally suitable to specifically address multidrug-resistant cancer.

In particular, the cobalt-polypyridyl complex comprising structures of Formulas (III), (IV) or (VII) and in particular essentially consisting of structures of Formulas (III), (IV) or (VII) and optionally a counterion proved to specifically and advantageously target P-glycoprotein-dependent multidrug-resistant and/or p53-deficient multidrug-resistant cancer cells through collateral sensitivity, i.e. it is especially suitable to selectively kill these multidrug-resistant cancer cells. Namely, a significantly lower dose is required for treating said multidrug-resistant cancer cells compared to cancer cells of the same cell type without a multidrug-resistant phenotype, usually the $IC_{50}$ of the cobalt-polypyridyl complex towards multidrug-resistant cancer cells is significantly reduced.

Summing up, the herewith provided class of cobalt-polypyridyl complexes shows highly promising anti-cancer effects and more importantly collateral sensitivity towards multidrug-resistant cancers.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is an immunofluorescence staining pattern obtained in the control group. FIG. 1B is an immunofluorescence staining pattern obtained under 5 µM of the cobalt-polypyridyl complex of Formula (IV) with $PF_6^-$ as counterion. FIG. 1C is an immunofluorescence staining pattern obtained under 10 µM of the cobalt-polypyridyl complex of Formula (IV) with $PF_6^-$ as counterion. FIG. 1D is an immunofluorescence staining pattern obtained under 20 µM of the cobalt-polypyridyl complex of Formula (IV) with $PF_6^-$ as counterion.

FIG. 3A shows the cell cycle progression of HeLa cancer cells of the control group. FIG. 3B shows the cell cycle progression of HeLa cancer cells treated with 5 µM of the cobalt-polypyridyl complex of Formula (IV) with $PF_6^-$ as counterion. FIG. 3C shows the cell cycle progression of HeLa cancer cells treated with 10 µM of the cobalt-polypyridyl complex of Formula (IV) with $PF_6^-$ as counterion. FIG. 3D shows the cell cycle progression of HeLa cancer cells treated with 15 µM of the cobalt-polypyridyl complex of Formula (IV) with $PF_6^-$ as counterion. FIG. 3E is a diagram showing the cell cycle progression results in HeLa cells of the control group and under the cobalt-polypyridyl complex of Formula (IV) with $PF_6^-$ as counterion (5 µM, 10 µM and 15 µM).

DESCRIPTION OF THE EMBODIMENTS

Figure 1A:
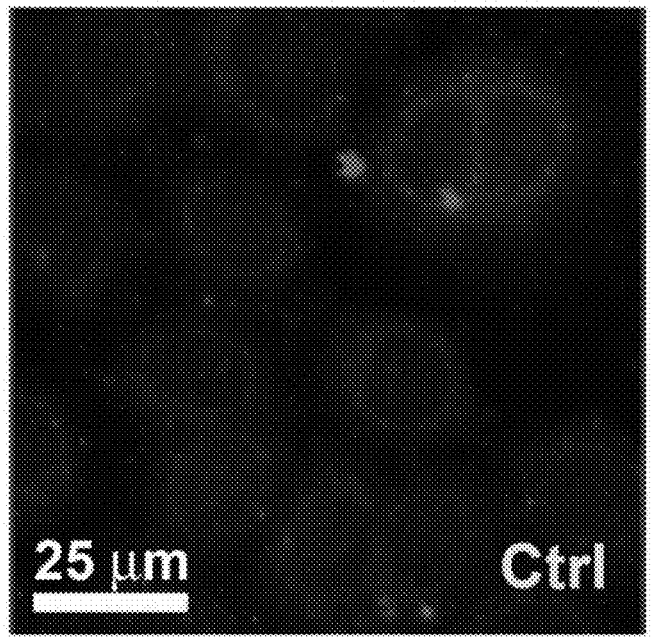
FIGS. 1A, 1B, 1C, and 1D refer to immunofluorescence staining patterns which show the endogenous LC3-II puncta formation in HeLa cancer cells under the cobalt-polypyridyl complex of Formula (IV) and in a control group.
Figure 1B:
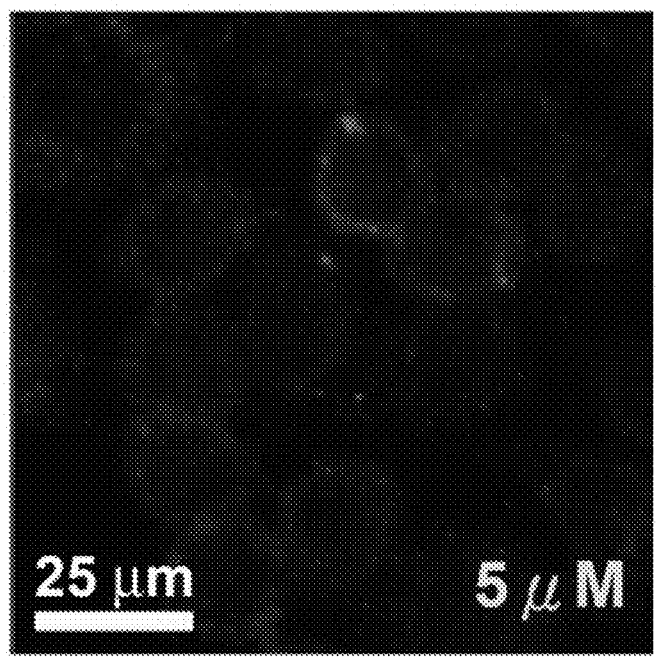
Figure 1C:
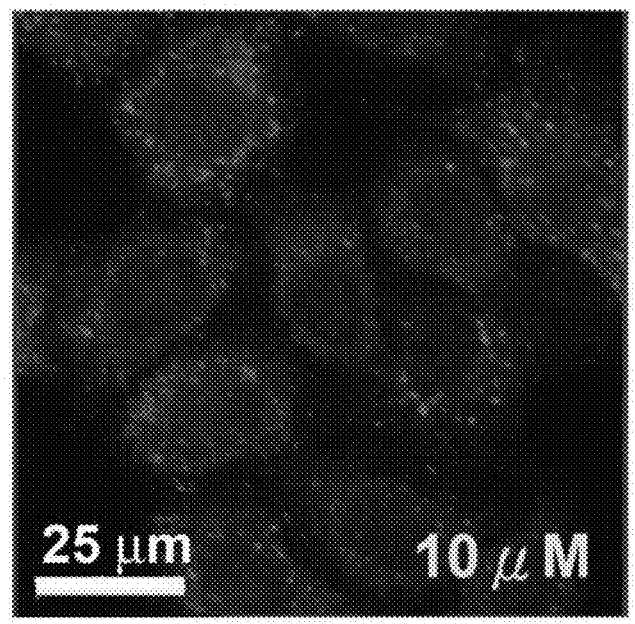
Figure 1D:
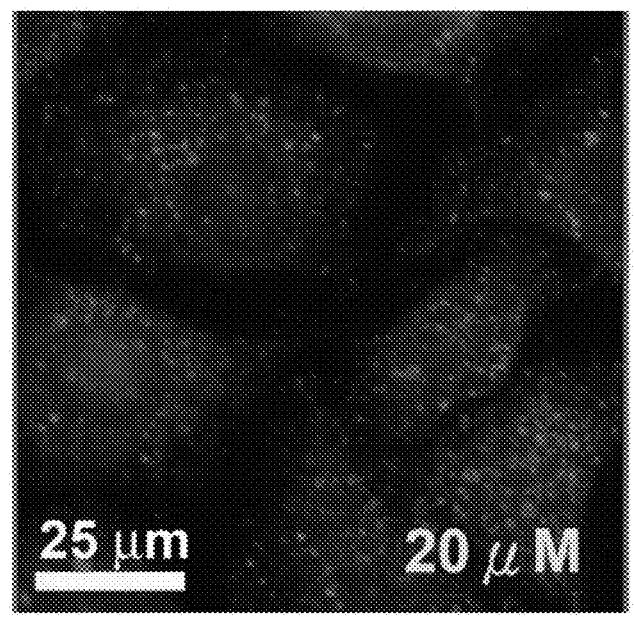
Figure 1E:
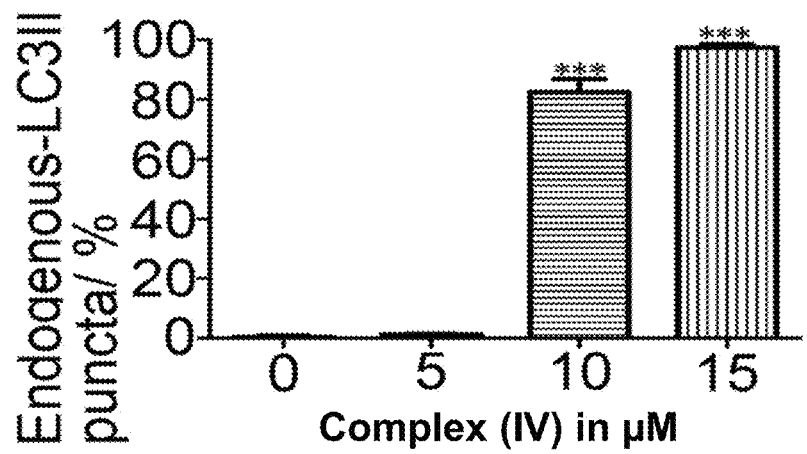
FIG. 1E is a diagram showing the endogenous LC3-II puncta formation under different doses of the cobalt-polypyridyl complex of Formula (IV) with $PF_6^-$ as counterion.

The following preparations and examples are given to enable those skilled in the art to more clearly understand and to practice the present invention. They should not be considered as limiting the scope of the invention, but merely as being illustrative and for representing preferred embodiments thereof. The technical terms used in the present patent application have the meaning as commonly understood by a respective skilled person unless specifically defined otherwise.

As used herein, "comprising" means including the following elements or structures but not excluding others. "Essentially consisting of" means that the material or compound consists of the respective element or structure along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention relates in a first aspect to a method for treating a subject suffering from cancer, in particular from a multidrug-resistant cancer, i.e. a cancer with multidrug-resistant phenotype. Said method of treating cancer comprises the step of administering an effective amount of a cobalt-polypyridyl complex to said subject.

The term "cobalt-polypyridyl complex" as used herein means a complex, i.e. a compound, formed by a cobalt ion and polypyridyl ligands including at least one of Formula (I) with $R^1$ and $R^2$ as described below and optionally comprising a counterion. Thus, the cobalt-polypyridyl complex does not comprise non-polypyridyl ligands or non-polypyridyl polymers. A polypyridyl ligand generally means a ligand having at least two pyridine rings covalently linked to each other, which may together form a larger ring system. Polypyridine ligands include, in particular, bipyridine, terpyridine and phenanthroline. The pyridine rings may optionally be substituted, in particular with alkyl or alkoxy groups such as $C_1$-$C_{10}$ alkyl or $C_1$-$C_{10}$ alkoxy groups. The cobalt-polypyridyl complex of the present invention comprises at least one polypyridyl ligand of Formula (I):

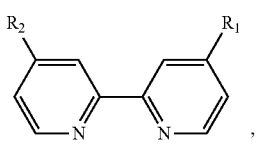

Formula (I)

wherein $R_1$ and $R_2$ are independently selected from hydrogen, a $C_1$-$C_{10}$ alkyl or a $C_1$-$C_{10}$ alkoxy, preferably from hydrogen, a $C_1$-$C_9$ alkyl or a $C_1$-$C_9$ alkoxy. Preferably, $R_1$ and $R_2$ are identical and most preferably selected from —H, —$CH_3$, —$C_9H_{19}$ or —$OCH_3$. Said ligand in particular acts as a bidentate ligand, i.e. both nitrogen atoms are coordinated to the cobalt ion.

The term "$C_1$-$C_{10}$ alkyl" as group used in the present invention refers to a hydrocarbyl radical having from 1 to 10 carbon atoms which includes a straight chain or branched alkyl group. Namely, it comprises, for example, methyl, ethyl, propyl, isopropyl, nonyl and so on. "$C_1$-$C_{10}$ alkoxy" refers to a radical having a formula -AB wherein A is an oxygen atom and B is $C_1$-$C_{10}$ alkyl, i.e. a straight chain or branched alkyl group with 1 to 10 carbon atoms, including for example methoxy and ethoxy. Preferably, the cobalt-polypyridyl complex comprises three ligands of Formula (I) coordinated to one cobalt ion, i.e. the cobalt-polypyridyl complex is a cobalt tris(bipyridine) system. The cobalt ion is preferably of the oxidation state +2 or +3. The cobalt ion is preferably octahedrally coordinated. In an octahedral coordination geometry, the ligands are coordinated to the cobalt ion in a symmetrical distribution, leading to the formation of an octahedron.

A counterion might affect the solubility or other chemical or physical properties of the cobalt-polypyridyl complex, wherein the exact nature of the counterion is not critical as long as it is pharmaceutically acceptable and/or not significantly toxic in the amounts used. Counterions can in particular be anions which are unlikely to bind directly to the cobalt ion of the cobalt-polypyridyl complex, i.e. non-coordinating anions. Non-coordination anions include, for example, hexafluorophosphate ($PF_6^-$), perchlorate ($ClO_4^-$) or tetrafluoroborate ($BF_4^-$). Examples of counterions, in particular, include hexafluorophosphate ($PF_6^-$) or chloride ($Cl^-$).

The term cobalt-polypyridyl complex encompasses any diastereomers and their mixtures, enantiomers and their mixtures such as racemates and salts of the cobalt-polypyridyl complex, in particular pharmaceutically acceptable salts. The skilled person is aware of such terms and how to isolate specific diastereomers or enantiomers. Likewise, the term cobalt-polypyridyl complex encompasses any solvates or hydrates of the cobalt-polypyridyl complex. The term "solvate" refers to a complex of variable stoichiometry formed by a solute, i.e. the cobalt-polypyridyl complex, and a solvent. If the solvent is water, the solvate formed is a hydrate.

The method of claim 1, wherein the cobalt-polypyridyl complex comprises a structure of Formula (II):

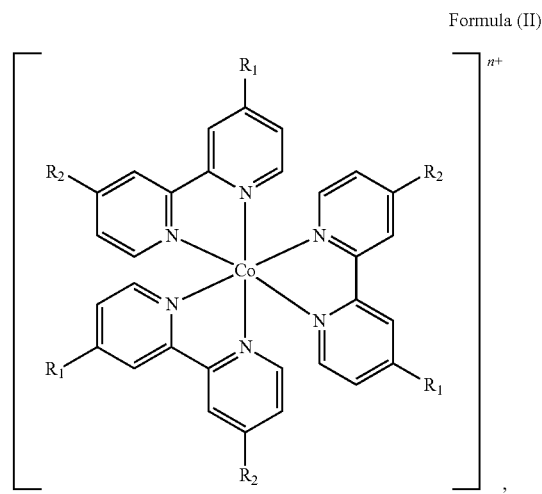

Formula (II)

wherein $R_1$ and $R_2$ are identical and as defined above. Preferably $R_1$ and $R_2$ are selected from —H, —$CH_3$, —$C_9H_{19}$ or —$OCH_3$. n corresponds to the oxidation state of the cobalt ion and is preferably 2 or 3. The cobalt-polypyridyl complex can optionally comprise a counterion which is preferably but not exclusively a monovalent anion selected from hexafluorophosphate ($PF_6^-$) or chloride ($Cl^-$).

More preferably, the cobalt-polypyridyl complex comprises and in particular essentially consists of a structure of one of Formulas (III), (IV), (V), (VI), (VII) or (VIII) and optionally a counterion, in particular a monovalent counterion preferably selected from, but not limited to, hexafluorophosphate ($PF_6^-$) or chloride ($Cl^-$):

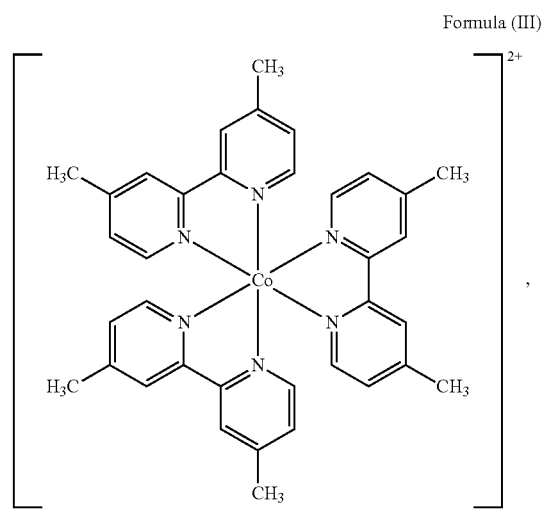

Formula (III)

Formula (IV)
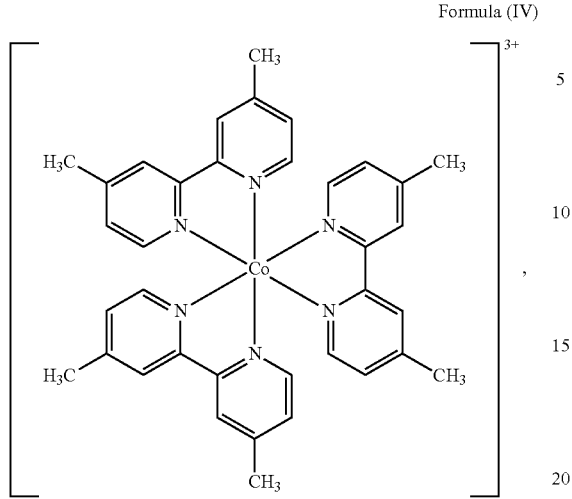
Formula (V)
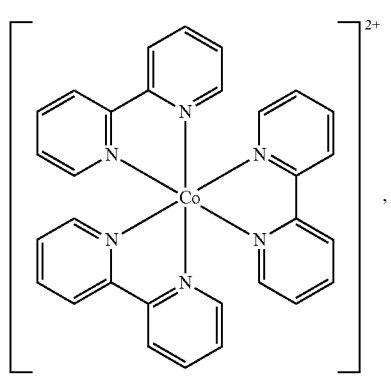
Formula (VI)
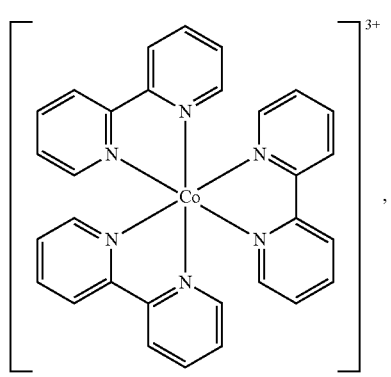
Formula (VII)
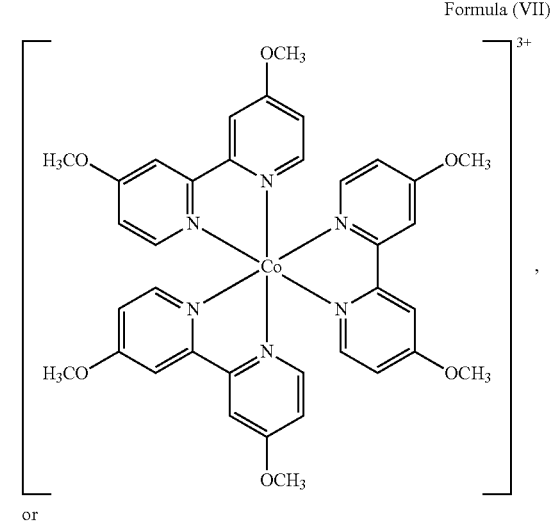
or
Formula (VIII)
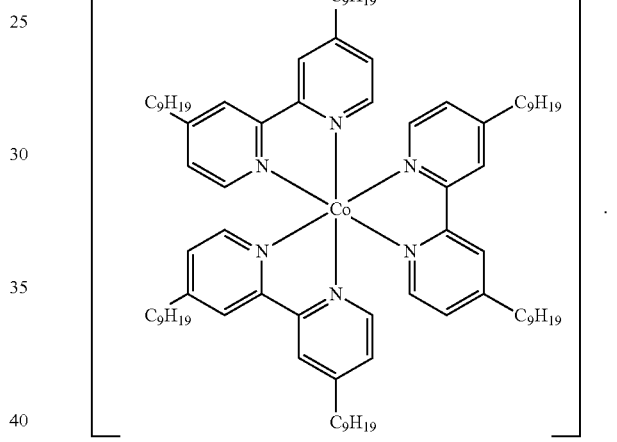
In further preferred embodiments, the cobalt-polypyridyl complex comprises and in particular essentially consists of a structure selected from Formula (III), Formula (IV) or Formula (VII) and optionally a counterion:
Formula (III)
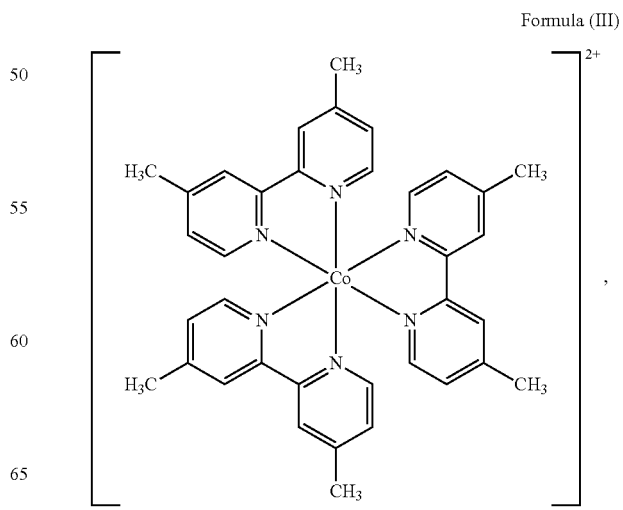

-continued

Formula (IV)

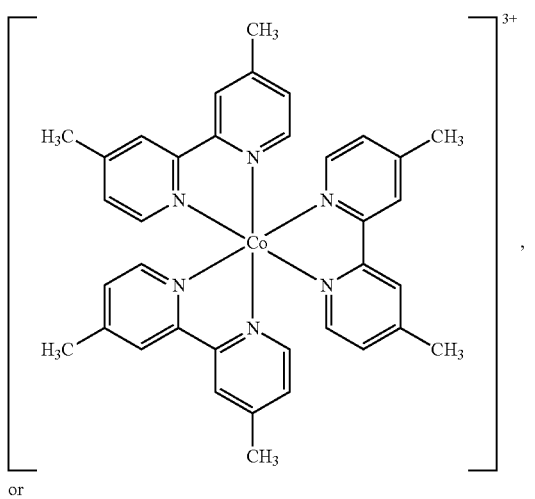

or

Formula (VII)

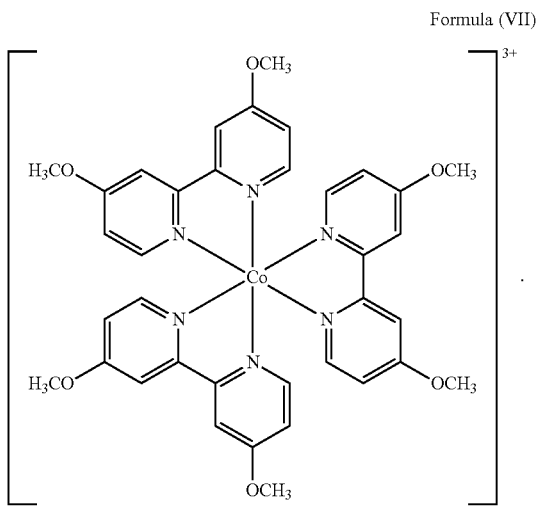

In most preferred embodiments of the present invention, the cobalt-polypyridyl complex comprises and in particular essentially consists of a structure of Formula (IV) and optionally a counterion:

Formula (IV)

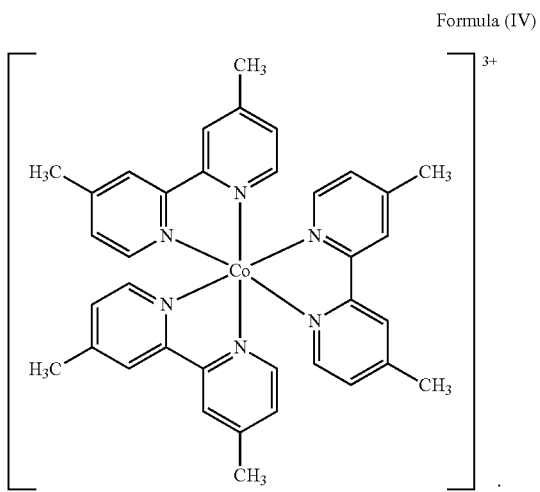

In particular embodiments of the present invention, the cobalt-polypyridyl complex comprises and in particular essentially consists of a structure of Formula (IV) and a counterion, wherein the counterion is a monovalent anion and preferably selected from, but not limited to, hexafluorophosphate ($PF_3^-$) or chloride ($Cl^-$).

The cobalt-polypyridyl complex may be administered in the method of the present invention in combination with:

(ii) an effective amount of at least one chemotherapeutic compound, which chemotherapeutic compound is a compound selected from the group consisting of a topoisomerase-II inhibitor, an anthracycline, a coordination complex of platinum, a taxane, a protein kinase inhibitor, a *vinca* alkaloid or derivative thereof, a topoisomerase-I inhibitor and a nucleotide analog or precursor analog;

(ii) radiotherapy, and/or (iii) immunotherapy.

The expression "effective amount" and "effective dose" generally denote an amount sufficient to produce therapeutically desirable results, wherein the exact nature of the result varies depending on the specific disorder which is treated. When the disorder is cancer, the result is usually an inhibition or suppression of the proliferation of the cancer cells, a reduction of cancerous cells or the amelioration of symptoms related to the cancer cells.

The effective amount of the cobalt-polypyridyl complex of the present invention may depend on the species, body weight, age and individual conditions of the subject and can be determined by standard procedures such as with cell cultures or experimental animals. A concentration of the cobalt-polypyridyl complex such as the cobalt-polypyridyl complex comprising a structure of Formula (IV) may, for example, be at least 1 μM, preferably at least 5 μM, in particular at least 10 μM or at least 20 μM.

The subject can be a human or animal, in particular the subject is a mammal, preferably a human. The subject is preferably a human having a cancer with a multidrug-resistance. Said subject, thus, includes human subjects having a drug resistance to conventional therapeutic agents which induce cell death in cancer cells, i.e. which are used to treat cancer.

The terms "cancer" and "cancerous" refer to or describe a physiological condition in subjects in which a population of cells are characterized by unregulated cell growth. The term "tumor" simply refers to a mass being of benign (generally harmless) or malignant (cancerous) growth.

The cancer can be of any origin, in particular human origin. In particular, the cancer is selected from the group consisting of:
 ovarian cancer,
 cervical cancer,
 liver cancer,
 lung cancer,
 breast cancer
 gastric cancer, or
 colon cancer.

Preferably, the cancer is selected from multidrug-resistant:
 lung cancer,
 breast cancer, or
 colon cancer
which is resistant at least against paclitaxel (taxol).

The provided method is preferably used and particularly effective in treating subjects whose cancer has become "multidrug-resistant". The term "multidrug-resistance" is generally used for an acquired or natural, i.e. intrinsic, resistance of a cancer.

Cancers with cancer cells that have developed resistance to or are naturally resistant to chemotherapeutic compounds, usually to two or more chemotherapeutic compounds, are said to be "multidrug-resistant" in the present patent application such as to chemotherapeutic compounds selected from the group consisting of topoisomerase-II inhibitors, anthracyclines, coordination complexes of platinum, taxanes, protein kinase inhibitors, *vinca* alkaloids or derivatives thereof, topoisomerase-I inhibitors and nucleotide analogs or precursor analogs. In preferred embodiments of the present invention, the multidrug-resistant cancer is a cancer having multidrug-resistant cancer cells, i.e. cancer cells which have developed resistance to or are naturally resistant to at least one of paclitaxel (taxol), doxorubicin, cisplatin, etoposide and staurosporine, in particular against one of taxol or cisplatin or both of them, more preferably cancer cells that are resistant at least against taxol.

A cancer is multidrug-resistant if it comprises cancer cells which are multidrug-resistant, in particular if a significant amount of the cancer cells, such as more than 50%, in said cancer are multidrug-resistant. Accordingly, the multidrug-resistant cancer will be less sensitive or more tolerant to most common chemotherapeutic agents.

A multidrug-resistance can be detected in a subject, cancer, tissue, or cell by administering to the subject, tissue, or cell, compounds such as chemotherapeutic compounds and determining the activity of the chemotherapeutic compounds such as the induction of cell death or the inhibition of the proliferation of cancer cells compared to a reference control, namely cells or tissue of the same cell or tissue type, a cancer or a subject that do not have multidrug-resistance or non-cancerous cells.

The multidrug-resistant cancer according to the present invention preferably has multidrug-resistant cancer cells which are at least one of:
"ABC-protein-dependent", i.e. the multidrug resistance is at least mediated by ABC transporter proteins (hereinafter "ABC-proteins"), in particular by P-glycoprotein, i.e. is associated with an enhanced expression and/or enhanced functional activity of at least one ABC-protein in the multidrug-resistant cancer cells, in particular of P-glycoprotein also referenced as "P-glycoprotein-dependent", and/or
"apoptosis-deficient", i.e. at least associated with a decreased expression of at least one pro-apoptotic protein and/or decreased pro-apoptotic activity of at least one pro-apoptotic protein and/or enhanced expression of at least one anti-apoptotic protein and/or enhanced anti-apoptotic activity of at least one anti-apoptotic protein in the multidrug-resistant cancer cells; in particular apoptosis-deficient refers to at least one of decreased expression of at least one pro-apoptotic protein and/or decreased pro-apoptotic activity of at least one pro-apoptotic protein, which pro-apoptotic protein is in particular p53 referenced herein as "p53-deficient".

In one embodiment of the present invention, the multidrug-resistance and hence the multidrug-resistant cancer is at least ABC-protein-dependent, in particular P-glycoprotein-dependent and/or apoptosis-deficient, in particular p53-deficient.

An enhanced expression and/or enhanced functional activity of at least one ABC-protein, i.e. ABC-protein-dependent multidrug-resistant cancer, means an expression and/or functional activity exceeding, in particular significantly exceeding, the one in normal cells or tissue, i.e. non-cancerous cells or tissue, or cancer cells without the multidrug-resistant phenotype. The term "enhanced expression" or "enhanced functional activity" of at least one ABC-protein such as P-glycoprotein includes embodiments in which the multidrug-resistant cancer cells express the ABC-protein such as P-glycoprotein, whereas in the reference control, i.e. cancer cells without the multidrug-resistant phenotype or non-cancerous cells of the same cell or tissue type, said ABC-protein such as P-glycoprotein is not expressed, at all. I.e. when said reference control does not express the ABC-protein such as P-glycoprotein, multidrug-resistant cancer cells having a detectable expression or functional activity of the ABC-protein such as P-glycoprotein are ABC-protein-dependent by definition.

Whether a multidrug-resistant cancer is an ABC-protein-dependent multidrug-resistant cancer can be determined by methods known to the skilled person in particular comprising immunological methods accompanied by the use of MDR-specific antibodies, immunocytochemistry and immunohistochemistry, respectively, by determining respective mRNA levels such as with Northern blots or quantitative RT-PCR, with MDR-specific antibodies in vivo or with an ABC-protein such as P-glycoprotein efflux assay detecting the efflux of a marker. In particular, an ABC-protein such as P-glycoprotein efflux assay can be used for determining the functional activity of ABC-proteins, i.e. for determining whether multidrug-resistant cancer cells are ABC-protein-dependent. Markers which can be used in said efflux assay include drugs which are a substrate for the respective ABC-protein, a radionuclide or a dye. In particular, a sample of multidrug-resistant cancer cells and, thus, a cancer having those cells, is preferably considered for being ABC-protein-dependent, if it comprises less cells with marker such as dye like Rho123 as revealed by the assay compared to the reference control which is a cell sample with ABC-protein expression as present in cancer cells that do not have a multidrug-resistance phenotype or non-cancerous cells of the same cell or tissue type.

Preferably, an ABC-protein-dependent such as a P-glycoprotein-dependent multidrug-resistant cancer is a cancer comprising multidrug-resistant cancer cells with an expression of ABC-protein or ABC-protein functional activity exceeding the one in the reference control by at least 10%, in particular by at least 20%. For example, the expression or functional activity of P-glycoprotein is at least 10% or at least 20% higher than the expression or functional activity of P-glycoprotein in the reference control.

The term "apoptosis-deficient" used herein refers to a cancer having at least one of (i) decreased expression and/or decreased pro-apoptotic activity of at least one pro-apoptotic protein or (ii) enhanced expression and/or enhanced anti-apoptotic activity of at least one anti-apoptotic protein or both of them, i.e. (i) and (ii). Pro- and/or anti-apoptotic proteins in particular include p53, mitogen-activated protein kinase (MAPK)-family members and B cell lymphoma 2 (Bcl-2) family members. In particular, "apoptosis-deficient" as used herein means at least a decreased expression and/or decreased pro-apoptotic activity of at least one pro-apoptotic protein selected from p53 or Bax or Bak of the Bcl-2-family. The term "p53 protein" used herein includes respective p53 isoforms encoded by the TP53 gene such as p53α, p53β, p53γ, Δ40p53α, Δ40p53β, Δ40p53γ, Δ133p53α, Δ133p53β, Δ133p53γ, Δ160p53α, Δ160p53β, Δ160p53γ and the like.

Whether a multidrug-resistant cancer is apoptosis-deficient can be determined by methods known to the skilled person, namely by measuring the expression of the pro-apoptotic protein and/or anti-apoptotic protein and/or by determining the apoptotic activity of the pro-apoptotic protein and/or the anti-apoptotic protein compared with a reference control, namely cancer cells that do not have a multidrug-resistance phenotype or non-cancerous cells of the same cell or tissue type. Suitable methods for determining the expression may include immunological methods accompanied by the use of specific antibodies, immunocytochemistry and immunohistochemistry, respectively, or by determining respective mRNA levels such as with Northern blots or quantitative RT-PCR. The apoptotic activity can be determined by assays which determine the rate of apoptosis known to the skilled person such as assays determining cytomorphological alterations, DNA fragmentation such as by TUNEL assay along with flow cytometry, detection of apoptosis pathway downstream targets, cleaved substrates, regulators and inhibitors, membrane alterations, or mitochondrial assays.

Decreased expression and/or decreased pro-apoptotic activity of pro-apoptotic proteins in particular means an expression and/or pro-apoptotic activity of said at least one protein which is decreased by at least 10%, more preferably by at least 20% compared with a reference control, namely cancer cells without the multidrug-resistant phenotype or non-cancerous cells of the same cell or tissue type. In particular embodiments of the present invention, said at least one pro-apoptotic protein is not detectably expressed in the multidrug-resistant cancer cells. Decreased expression and/or decreased pro-apoptotic activity of at least one pro-apoptotic protein may be caused by, for example, a decreased expression of pro-apoptotic wild-type protein and/or by an expression of a pro-apoptotic mutant protein with decreased pro-apoptotic activity. A mutant pro-apoptotic protein has an amino acid sequence different from the wild-type protein expressed in healthy cells without a mutation in the respective encoding genes.

In an embodiment of the present invention, the multidrug-resistant cancer is a cancer comprising at least one of:
  multidrug-resistant apoptosis-deficient cancer cells with a decreased expression and/or decreased pro-apoptotic activity of p53, and/or
  multidrug-resistant P-glycoprotein-dependent cancer cells,
in particular comprising a significant amount of such cancer cells.

The method of the present invention may comprise further steps before administering the cobalt-polypyridyl complex, in particular the cobalt-polypyridyl complex of Formula (III), (IV) or (VII) of:
  obtaining a sample, in particular cancer cells, from the subject;
  testing said sample for at least one of
  the expression of at least one ABC-protein, in particular of P-glycoprotein;
  at least one ABC-protein, in particular the P-glycoprotein, functional activity;
  the expression of at least one pro- or anti-apoptotic protein, in particular p53;
  the apoptotic activity of at least one pro- or anti-apoptotic protein, in particular of p53;
  optionally correlating the expression and/or functional activity of the at least one ABC-protein and/or the expression or activity of the at least one pro- or anti-apoptotic protein with an outcome and if conditions are met, administering the cobalt-polypyridyl complex to said subject; alone or in combination with a further chemotherapeutic compound.

According to the invention is also the cobalt-polypyridyl complex of the present invention, in particular comprising a structure of Formula (III), (IV) or (VII), for use as a medicament for the treatment of cancer, in particular multidrug-resistant cancer such as P-glycoprotein dependent multidrug-resistant cancer or p53-deficient multidrug-resistant cancer. The cobalt-polypyridyl complex of the present invention, in particular comprising a structure of Formula (III), (IV) or (VII), can be used in an effective amount for treating an animal or a human, in particular mammal, preferably a human. Another aspect of the invention refers to the use of the cobalt-polypyridyl complex of the present invention, in particular comprising a structure of Formula (III), (IV) or (VII), for preparing a medicament for treatment of cancer, in particular multidrug-resistant cancer such as P-glycoprotein-dependent cancer or p53-deficient multidrug-resistant cancer. The cobalt-polypyridyl complex of the present invention, in particular comprising a structure of Formula (III), (IV) or (VII), may be used in combination with at least a further chemotherapeutic compound.

The present invention also relates to a method of using the cobalt-polypyridyl complex of the present invention, preferably comprising and in particular essentially consisting of a structure of Formula (III), (IV) or (VII) and optionally a counterion, for suppressing cancer growth, in particular for inducing autophagy, inducing cell cycle arrest and/or inhibiting cell invasion.

The suppression of cancer growth, in particular induction of autophagy, induction of cell cycle arrest and inhibition of cell invasion can be determined with an immunofluorescence staining with anti-LC3 antibodies or Western Blotting of LC3-I and LC3-II, the latter being a marker for autophagy. Cell cycle analysis can be carried out, for example, with DNA-binding dyes such as propidium bromide. Inhibition of cell invasion can be examined with commercially available cell invasion assay kits. The measurements are carried out in the presence of the cobalt-polypyridyl complex of the present invention compared to a reference control being cancerous cells of the same cell type in the absence of the cobalt-polypyridyl complex. A suppression of cancer growth, in particular induction of autophagy, induction of cell cycle arrest and inhibition of cell invasion means a statistically significant change compared to the reference control, preferably more than 10% and in particular more than 20% change compared to the value measured for the reference control.

The cobalt-polypyridyl complex of the present invention comprising a cobalt ion in the oxidation state +2 or +3, at least one polypyridyl ligand of Formula (I) and optionally a counterion can be prepared by a method comprising steps of:
(i) providing a mixture of a cobalt salt with a cobalt oxidation state of +2 and the polypyridyl ligand of Formula (I):

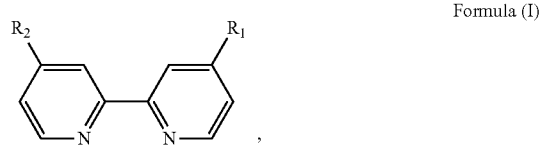

Formula (I)

in a solvent, wherein $R_1$ and $R_2$ are independently selected from hydrogen, a $C_1$-$C_{10}$ alkyl or a $C_1$-$C_{10}$ alkoxy and optionally a further polypyridyl ligand;
(ii) optionally adding a salt comprising the counterion;
(iii) optionally oxidizing the cobalt ion to the oxidation state +3.

The solvent in step (i) preferably comprises an aliphatic alcohol, which means herein an aliphatic hydrocarbon, preferably a branched or straight chain alkane, wherein at least one hydrogen atom of the aliphatic hydrocarbon is substituted with a hydroxyl group, preferably one hydrogen atom is substituted with a hydroxyl group referenced as monohydric aliphatic alcohol. More preferably, the aliphatic alcohol is a monohydric aliphatic alcohol, still more preferably a monohydric alcohol with 1 to 3 carbon atoms, further preferably with 1 to 2 carbon atoms. I.e. the aliphatic alcohol is more preferably selected from methanol, ethanol, propanol or isopropanol or mixtures thereof and further preferably from methanol, ethanol or mixtures thereof. More preferably, the aliphatic alcohol is methanol. The solvent in step (i) most preferably essentially consists of methanol.

Step (i) preferably comprises steps of:
a) preparing a mixture of the cobalt salt with a cobalt oxidation state of +2 and the polypyridyl ligand of Formula (I) in methanol; wherein the molar ratio of the polypyridine ligand of Formula (I) and the cobalt salt is between 2:1 and 4:1, more preferably about 3.3:1;
b) heating the mixture to reflux, preferably under $N_2$ atmosphere for 1 h to 3 h, preferably for about 2 h;
c) cooling the mixture down to a temperature between 20° C. and 30° C., preferably to about 25±2° C.

The cobalt salt is preferably a cobalt chloride or hydrate thereof, more preferably $CoCl_2 \times 6\,H_2O$. The ligand is preferably of Formula (I) with $R_1$ and $R_2$ being identical and selected from —H, —$CH_3$, —$C_9H_{19}$, —$OCH_3$. Preferably, no further polypyridyl ligand is added in step (i).

Step (ii) preferably comprises adding an excess of a salt comprising the counterion, preferably monovalent anions which are in particular, but not exclusively, selected from $PF_6^-$ or $Cl^-$, for example, adding $NH_4PF_6$. Step (ii) in particular comprises steps of:
a) adding the salt comprising the counterion, in particular in a molar ratio of at least 4:1 compared to the cobalt salt added in step (i);
b) stirring the mixture for 30 min to 90 min, in particular for about 60 min;
c) separating the precipitate by filtration and optional purifying the precipitate and optional drying.

Purification in step c) may be carried out by washing with at least one washing solvent, in particular an aliphatic alcohol and/or an ether, still more preferably a monohydric alcohol with 1 to 3 carbon atoms, further preferably with 1 to 2 carbon atoms and/or an ether, in particular a $C_2$ to $C_6$ dialkyl ether. More preferably, the at least one washing solvent is selected from one or more of methanol, ethanol or diethyl ether. The optional drying may be carried out in vacuum.

Step (iii) preferably comprises steps of:
a) adding an oxidizing agent and a solvent;
b) removing the solvent for obtaining a residue;
c) optionally dissolving the residue in a solvent and adding a salt comprising the counterion;
d) separating the precipitate by filtration and optionally purifying the precipitate and optionally drying.

The oxidizing agent is preferably $NOBF_4$ and used in a molar ratio to the cobalt complex obtained in step (i) of between 0.8:1 and 1.2:1, in particular of about 1:1. The solvent is preferably an organic nitrile, in particular acetonitrile. The mixture in step a) is preferably left at a temperature of between 20° C. and 30° C., preferably about 25±2° C. for about 1 h. The solvent is preferably removed under reduced pressure. The solvent in step c) is preferably an organic nitrile, more preferably acetonitrile. Step c) preferably comprises adding an excess of a salt comprising the counterion, preferably but not exclusively monovalent anions in particular selected from $PF_6^-$ or $Cl^-$, for example, adding $NH_4PF_6$, in particular with a molar ratio of at least 4:1 compared to the cobalt complex obtained in step (i). Purifying the precipitate is preferably carried out by recrystallizing the precipitate in a recrystallization solvent comprising a ketone and/or an ether, preferably acetone and/or diethyl ether. Drying may be carried out in vacuum. If desired, a counterion can be readily exchanged with another counterion by any of the methods known to one skilled in the art, including ion exchange chromatography and other ion exchange methods or recrystallization.

The present invention further provides a method for suppressing the growth of cancer cells comprising contacting the cancer cells with an effective amount of a cobalt-polypyridyl complex, wherein the cobalt-polypyridyl complex comprises a cobalt ion and at least one polypyridyl ligand of Formula (I):

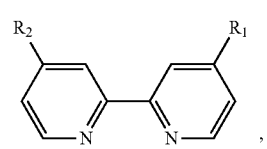

Formula (I)

wherein $R_1$ and $R_2$ are independently selected from hydrogen, a $C_1$-$C_{10}$ alkyl or a $C_1$-$C_{10}$ alkoxy. Preferably, the method is for inducing autophagy of the cancer cells, inducing cell cycle arrest of the cancer cells and/or inhibiting cell invasion of the cancer cells.

The cancer cells are preferably multidrug-resistant cancer cells and more preferably at least one of (i) multidrug-resistant ABC-protein-dependent, in particular P-glycoprotein-dependent multidrug-resistant cancer cells and/or (ii) apoptosis-deficient multidrug-resistant cancer cells, in particular p53-deficient multidrug-resistant cancer cells. The multidrug-resistant cancer cells are preferably at least resistant against taxol. The Resistant Factor of the cobalt-polypyridyl complex towards the multidrug-resistant cancer cells is preferably less than 0.6.

The $IC_{50}$ of the cobalt-polypyridyl complex against the cancer cells is preferably at most 10 µM with an $IC_{50}$ against non-cancerous cells at least 2 times higher. The cancer cells are preferably of human origin. The cancer cells are preferably from one of:
an ovarian cancer,
a cervical cancer,
a liver cancer,
a lung cancer,
a breast cancer,
a gastric cancer, or
a colon cancer.

The concentration of the cobalt-polypyridyl complex used for contacting the cancer cells may range from 0.2 µM to 100 µM, preferably from 1 µM to 30 µM, i.e. from 1 µmol/l (=1 mmol/m³) and 30 µmol/l (=30 mmol/m³). The cancer cells are preferably contacted with the cobalt-polypyridyl complex of the present invention for at least 12 h, preferably for at least 24 h, more preferably for at least 48 h and in particular for at least 72 h.

In especially preferred embodiments of the present invention, the cobalt-polypyridyl complex used for contacting the cancer cells comprises and in particular essentially consists of a structure of Formula (III), (IV) or (VII) and optionally a counterion:

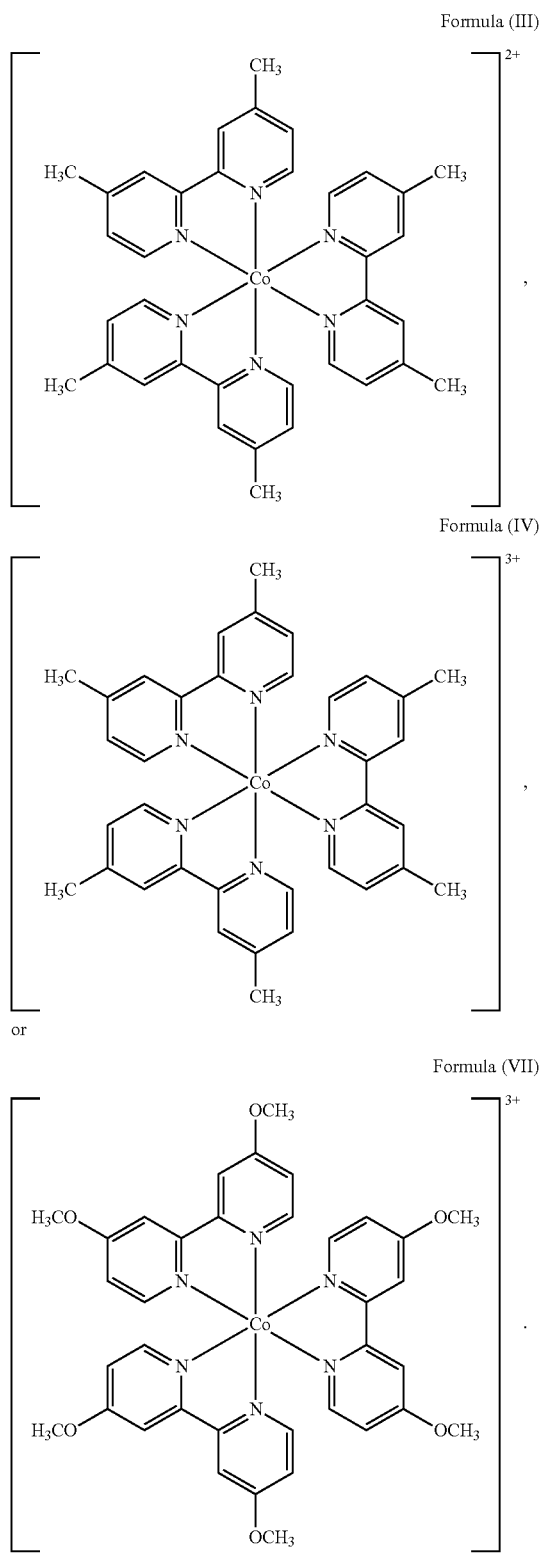

or

The cobalt-polypyridyl complex more preferably comprises a structure of Formula (IV), wherein the cancer cells are contacted with of from about 1 µM to about 30 µM of said cobalt-polypyridyl complex. In particular embodiments of the present invention, the cobalt-polypyridyl complex comprises and in particular essentially consists of a structure of Formula (IV) and optionally a counterion. The counterion can be a monovalent anion and preferably but not exclusively selected from hexafluorophosphate ($PF_6^-$) or chloride ($Cl^-$) and wherein the cancer cells are contacted with of from about 1 µM to about 30 µM of said cobalt-polypyridyl complex. The step of contacting the cancer cells with the cobalt-polypyridyl complex of the present invention, in particular comprising a structure of Formula (III), (IV) or (VII), may be carried out by applying an incubation solution comprising the cobalt-polypyridyl complex to said cells which incubation solution may further comprise suitable excipients such as buffers or a suitable growth medium.

The method may further comprise contacting said cells with a further chemotherapeutic compound; including for example, cisplatin, doxorubicin, taxol, etoposide and staurosporine; before, at the same time with or subsequent to the application of the cobalt-polypyridyl complex of the present invention.

In another aspect of the present invention, a method for specifically targeting cancer cells with multidrug-resistance is provided, in particular ABC-protein-dependent multidrug-resistant cancer cells such as P-glycoprotein dependent multidrug-resistant cancer cells or apoptosis-deficient such as p53-deficient multidrug-resistant cancer cells. Said method comprises the step of contacting a population of cancer cells with multidrug-resistance such as in a sample from a subject or in a subject with the cobalt-polypyridyl complex described above. Preferably, the cancer growth is suppressed, in particular autophagy is induced, cell cycle arrest is induced and/or cell invasion is inhibited.

The multidrug-resistant cancer cells are in particular ABC-protein-dependent, most preferably P-glycoprotein-dependent and/or apoptosis-deficient such as p53-deficient.

The multidrug-resistant cancer cells can be of any origin, in particular human origin. In particular, the multidrug-resistant cancer cells are from a multidrug-resistant:
ovarian cancer,
cervical cancer,
liver cancer,
lung cancer,
breast cancer
gastric cancer, or
colon cancer.

In preferred embodiments of the present invention, the multidrug-resistant cancer cells are resistant against at least one of paclitaxel (taxol), doxorubicin, cisplatin, etoposide and staurosporine, in particular against at least taxol.

The concentration of the cobalt-polypyridyl complex used for contacting the multidrug-resistant cancer cells may range from 0.2 µM to 100 µM, preferably from 1 µM to 30 µM, i.e. from 1 µmol/l (=1 mmol/m³) and 30 µmol/l (=30 mmol/m³). The multidrug-resistant cancer cells are preferably contacted with the cobalt-polypyridyl complex of the present invention for at least 12 h, preferably for at least 24 h, more preferably for at least 48 h and in particular for at least 72 h.

Preferably, the $IC_{50}$ of the cobalt-polypyridyl complex towards the multidrug-resistant cancer cells is at most 20 µM, more preferably at most 15 µM and in particular at most 5 µM. The Resistant Factor of the cobalt-polypyridyl complex of the present invention towards the multidrug-resistant cancer cells is preferably less than 0.8, more preferably less than 0.6 and in particular less than 0.5 and more preferably less than 0.3. The Resistant Factor is calculated by dividing the $IC_{50}$ of the cobalt-polypyridyl complex towards multidrug-resistant cells by its $IC_{50}$ towards cancer cells of the same cell type or tissue which do not have a multidrug-resistance phenotype. A Resistant Factor <1 indicates that a compound is especially effective in multidrug-resistant cancer cells compared to cancer cells of the same cell type or tissue which do not have a multidrug-resistant phenotype, i.e. is especially suitable to specifically target multidrug-resistant cancer cells.

In one embodiment of the present invention, the multidrug-resistant cancer cells used within the method are P-glycoprotein-dependent multidrug-resistant cancer cells and the Resistant Factor of the cobalt-polypyridyl complex of the present invention is at most 0.5, wherein the multidrug-resistant cancer cells are from a lung cancer, colon cancer or breast cancer and wherein the multidrug-resistant cancer cells are resistant against taxol.

In another embodiment of the present invention, the multidrug-resistant cancer cells used within the method are p53-deficient multidrug-resistant cancer cells and wherein the Resistant Factor of the cobalt-polypyridyl complex of the present invention is at most 0.6 and wherein the multidrug-resistant cancer cells are from a colon cancer.

In especially preferred embodiments of the present invention, the cobalt-polypyridyl complex used for contacting the multidrug-resistant cancer cells comprises and in particular essentially consists of a structure of Formula (III), (IV) or (VII) and optionally a counterion:

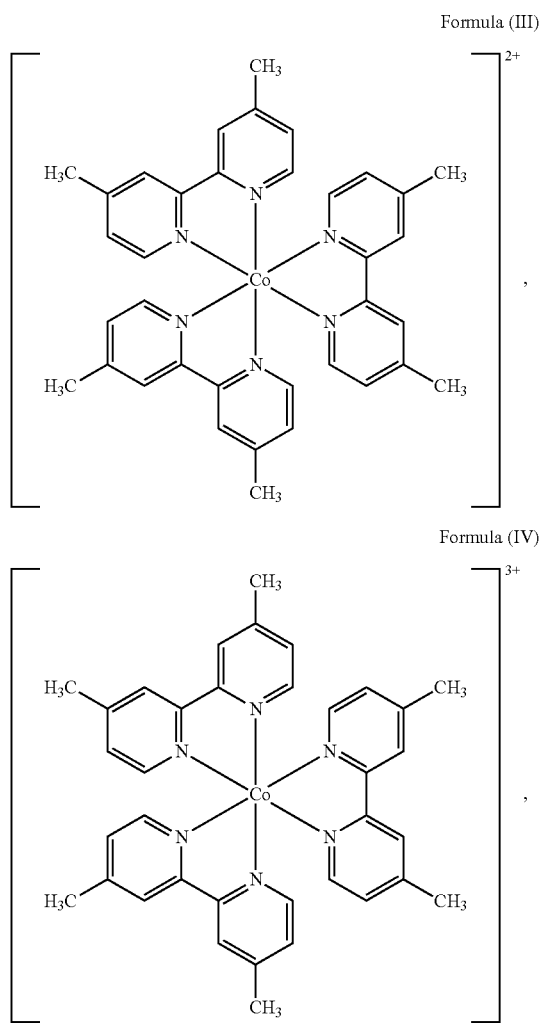

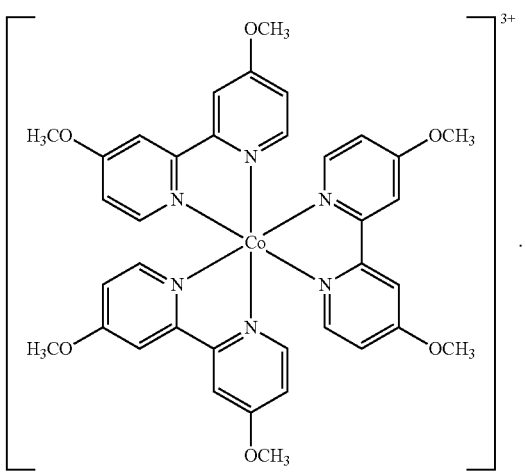

The cobalt-polypyridyl complex more preferably comprises a structure of Formula (IV) and optionally a counterion, wherein the multidrug-resistant cancer cells are contacted with of from about 1 μM to about 30 μM of said cobalt-polypyridyl complex. In particular embodiments of the present invention, the cobalt-polypyridyl complex comprises and in particular essentially consists of a structure of Formula (IV) and optionally a counterion. The counterion can be a monovalent anion and preferably but not exclusively be selected from hexafluorophosphate ($PF_6^-$) or chloride ($Cl^-$).

The step of contacting the cancer cells with the cobalt-polypyridyl complex of the present invention, in particular comprising a structure of Formula (III), (IV) or (VII), may be carried out by applying an incubation solution comprising the cobalt-polypyridyl complex to said cells which incubation solution may further comprise suitable excipients such as buffers or a suitable growth medium.

The method may further comprise contacting said cells with a further chemotherapeutic compound; including for example, cisplatin, doxorubicin, taxol, etoposide and staurosporine; before, at the same time with or subsequent to the application of the cobalt-polypyridyl complex of the present invention.

Further in accordance with the present invention is a composition comprising the cobalt-polypyridyl complex and an excipient such as selected from a pharmaceutically acceptable carrier, salt, buffer, water, or a combination thereof. More preferably, the composition is a pharmaceutical composition comprising an effective dose of the cobalt-polypyridyl complex and at least one pharmaceutically tolerable excipient such as selected from at least one of a diluent, a filler, a binder, a disintegrant, a lubricant, a coloring agent, a surfactant or a preservative.

The skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition. The pharmaceutical composition according to the invention can be present in solid, semisolid or liquid form to be administered by an oral, rectal, topical, parenteral or transdermal or inhalative route to a subject, preferably a human.

Further in accordance with the present invention is a kit comprising an effective dose of:

(i) a cobalt-polypyridyl complex as described above;

(ii) at least one chemotherapeutic compound selected from the group consisting of a topoisomerase-II inhibitor, an anthracycline, a coordination complex of platinum, a taxane, a protein kinase inhibitor, a *vinca* alkaloid or derivative thereof, a topoisomerase-I inhibitor and a nucleotide analog or precursor analog.

The kit may comprise excipients, in particular pharmaceutically tolerable excipients, such as a carrier, salt, buffer, water, or a combination thereof. The skilled person is able to select suitable excipients. Still further, the kit may comprise at least one container.

Preferably, the cobalt-polypyridyl complex in the pharmaceutical composition or the kit comprises and in particular essentially consists of a structure of Formula (III), (IV) or (VII) and optionally a counterion:

Formula (III)

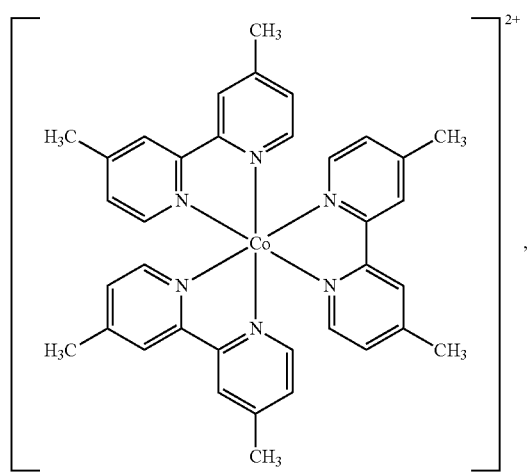

Formula (IV)

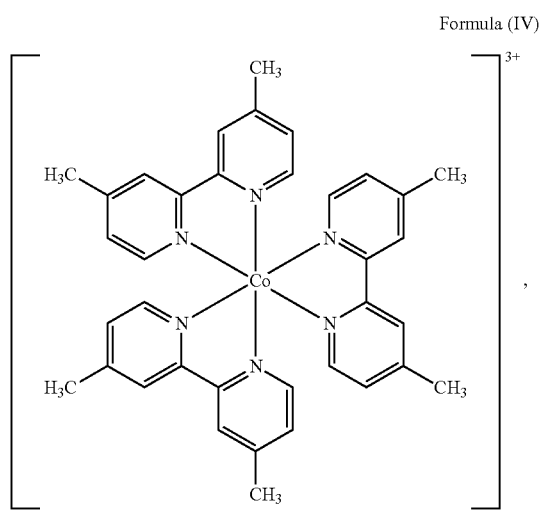

or

Formula (VII)

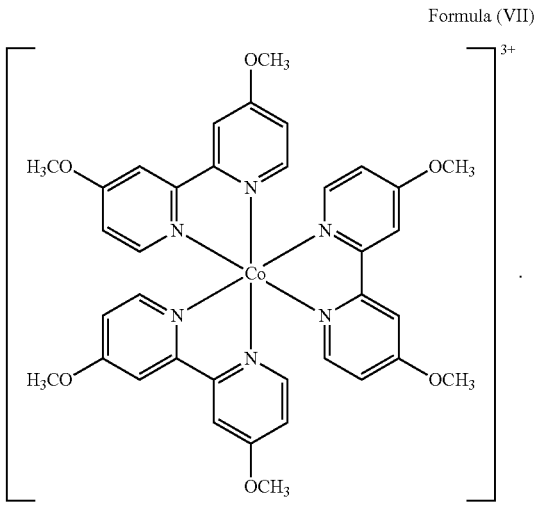

The cobalt-polypyridyl complex more preferably comprises a structure of Formula (IV). In particular embodiments of the present invention, the cobalt-polypyridyl complex comprises and in particular essentially consists of a structure of Formula (IV) and optionally a counterion, which can be a monovalent anion and preferably but not exclusively be selected from hexafluorophosphate ($PF_6^-$) or chloride ($Cl^-$).

Still another aspect of the present invention concerns the use of the pharmaceutical composition or the kit described above for suppressing the growth of cancer cells, in particular multidrug-resistant cancer cells, more preferably for inducing autophagy of the cancer cells, inducing cell cycle arrest of the cancer cells and/or inhibiting cell invasion of the cancer cells.

EXAMPLES

Example 1

Preparation of Cobalt-Polypyridyl Complexes of the Present Invention

Cobalt-polypyridyl complexes of Formula (V) and (VI) with a counterion were synthesized according to the method below. Other cobalt-polypyridyl complexes were prepared by the modification of the reported procedure.

Preparation of $[Co^{II}(N^\frown N)_3](PF_6)_2$ (Cobalt-Polypyridyl Complex of Formula (V) with $PF_6^-$ as Counterion)

A mixture of $CoCl_2 \cdot 6H_2O$ (4 mmol) and 2,2'-bipyridine (13.2 mmol) in methanol (100 mL) was heated to reflux under $N_2$ for 2 h. After cooling down to room temperature, $NH_4PF_6$ (20 mmol) was added to the reaction mixture and the reaction mixture was stirred for another 1 h. The precipitate was filtrated and washed with methanol and then diethyl ether.

Preparation of $[Co^{III}(N^\frown N)_3](PF_6)_3$ (Cobalt-Polypyridyl Complex of Formula (VI) with $PF_6^-$ as Counterion)

Oxidation of $[Co^{II}(N^\frown N)_3](PF6)_2$ (2 mmol) was carried out by the treatment of $NOBF_4$ (2 mmol) in acetonitrile (40 mL) at room temperature for 1 h. After removing the solvent under reduced pressure, the residue was dissolved in acetonitrile (10 mL) and $NH_4PF_6$ (10 mmol) was added. The precipitate was collected by filtration and the solid was purified by recrystallization of acetone/diethyl ether to afford the crystal form of the desired product.

[$Co^{II}$(4,4'-$Me_2$-Bpy)$_3$](PF$_6$)$_2$ (Cobalt-Polypyridyl Complex of Formula (III) with PF$_6^-$ as Counterion)

This complex has been obtained as yellow solid in 95% yield. Positive-ion ESI-MS ion cluster at m/z (%): 756.20 [M-PF$_6^-$]$^+$. IR (KBr) v/cm$^{-1}$: 843 (PF$_6^-$). Anal. Calcd for CoH$_{36}$H$_{36}$N$_6$F$_2$P$_{12}$.H$_2$O (%): C, 47.02; H, 4.17; N, 9.14. Found: C, 46.88; H, 4.14; N, 9.13.

[$Co^{III}$(4,4'-$Me_2$-Bpy)$_3$.](PF$_6$)$_3$ (Cobalt-Polypyridyl Complex of Formula (IV) with PF$_6^-$ as Counterion)

This complex has been obtained as yellow crystals in 88% yield (through two steps). $^1$H NMR (300 MHz, DMSO-$d_6$, 298K, TMS)/ppm: δ 8.91 (s, 2H, H3 of bpy), 7.61 (d, 2H, J=4.8 Hz, H6 of bpy), 7.27 (d, 2H, J=4.8 Hz, H5 of bpy), 2.63 (s, 6H, CH$_3$). $^{13}$C NMR (75 MHz, DMSO-$d_6$, 298K, TMS)/ppm: δ 156.7, 155.2, 150.4, 132.2, 127.9, 21.5. IR (KBr) v/cm$^{-1}$: 853 (PF$_6^-$). Positive-ion ESI-MS ion cluster at m/z 901.2 [M-PF$_6^-$]$^+$, 305.6 [M-2×PF$_6^-$]$^{2+}$, 302.7 [M-3× PF$_6^-$]$^{3+}$. Anal. Calcd for CoH$_{36}$H$_{36}$N$_6$F$_3$P$_{18}$.MeOH (%): C, 41.20; H, 3.74; N, 7.79. Found: C, 41.09; H, 4.09; N, 7.82.

[$Co^{III}$(4,4'-(OMe)$_2$-Bpy)$_3$](PF$_6$)$_3$ (Cobalt-Polypyridyl Complex of Formula (VII) with PF$_6^-$ as Counterion)

This complex has been obtained as orange crystals in 87% yield (through two steps). $^1$H NMR (300 MHz, DMSO-$d_6$, 298K, TMS)/ppm: δ 8.68 (s, 2H, H3 of bpy), 7.32 (d, 2H, J=5.1 Hz, H6 of bpy), 7.21 (d, 2H, J=5.1 Hz, H5 of bpy), 4.09 (s, 6H, OCH$_3$). $^{13}$C NMR (75 MHz, DMSO-$d_6$, 298K, TMS)/ppm: δ 170.6, 156.8, 151.6, 117.4, 114.1, 58.2. IR (KBr) v/cm$^{-1}$: 845 (PF$_6^-$). Positive-ion ESI-MS ion cluster at m/z 997.1 [M-PF$_6^-$]$^+$, 426.1 [M-2×PF$_6^-$]$^+$, 235.7 [M-3× PF$_6^-$]$^+$. Anal. Calcd for CoH$_{36}$H$_{36}$O$_6$N$_6$F$_3$P$_{18}$.2H$_2$O (%): C, 36.39; H, 3.42; N, 7.13. Found: C, 36.66; H, 3.50; N, 7.24.

[$Co^{III}$(4,4'-($C_9H_{19}$)$_2$-Bpy)$_3$](PF$_6$)$_3$ (Cobalt-Polypyridyl Complex of Formula (VIII) with PF$_6^-$ as Counterion)

This complex has been obtained as yellow crystals in 85% yield (through two steps). $^1$H NMR (300 MHz, DMSO-$d_6$, 298K, TMS)/ppm: δ 8.95 (s, 2H, H3 of bpy), 7.64 (d, 2H, J=4.8 Hz, H6 of bpy), 7.24 (d, 2H, J=4.8 Hz, H5 of bpy), 2.88 (t, 4H, J=5.7 Hz, CH$_2$), 1.71-1.67 (m, 4H, CH$_2$), 1.31-1.20 (m, 24H, CH$_2$), 0.87 (t, 6H, J=5.1 Hz, CH$_3$). $^{13}$C NMR (75 MHz, DMSO-$d_6$, 298K, TMS)/ppm: δ 160.6, 155.5, 150.8, 131.3, 127.2, 35.0, 31.7, 29.7, 29.4, 29.2, 29.1, 22.6, 14.4.IR (KBr) v/cm$^{-1}$: 835 (PF$_6^-$). Positive-ion ESI-MS ion cluster at m/z 1574.9 [M-PF$_6^-$]$^+$, 714.5 [M-2× PF$_6^-$]$^{2+}$, 428.0 [M-3×PF$_6^-$]$^{3+}$. Anal. Calcd for CoH$_{84}$H$_{132}$N$_6$F$_3$P$_{18}$.CH$_3$CH$_2$OCH$_2$CH$_3$ (%): C, 58.92; H, 7.98; N, 4.68. Found: C, 59.03; H, 7.93; N, 4.65.

Example 2

Cytotoxicity Assays

All prepared cobalt-polypyridyl complexes were dissolved in DMSO at a final concentration of 50 mmol/L and stored at −20° C. before use. Cytotoxicity was assessed by using the 3-(4,5-dimethylthiazol-2-yl)-2,5-diphenyltetrazolium bromide (MTT) (5.0 mg/ml) assay as previously described (Wong, V. K. et al., Cell Death Dis, 2013, 4, e720). Briefly, 4×10$^3$ cells per well were seeded in 96-well plates before drug treatments. After overnight culture, the cells were then exposed to different concentrations of selected compounds (0.039-100 μmol/L) for 72 h. Cells without drug treatment were used as control. Subsequently, MTT (10 μL) solution was added to each well and incubated at 37° C. for 4 h followed by the addition of 100 μL solubilization buffer (10% SDS in 0.01 mol/L HCl) and overnight incubation. A$_{570}$ nm was then determined in each well on the next day. The percentage of cell viability was calculated using the following formula: Cell viability (%)=A$_{treated}$/A$_{control}$×100. Data were obtained from three independent experiments. Cells include HeLa cells (cervical cancer), MCF-7 (breast cancer), H1299, H1975, A549 and LLC-1 (lung cancer), HepG2 and Hep3B (liver cancer) and LO2 (normal human hepatocytes).

The prepared cobalt-polypyridyl complexes displayed considerable cytotoxicity against cancer cells from different origins. Among the six cobalt-polypyridyl complexes, the cobalt-polypyridyl complexes of Formula (III), (IV) and (VII) (with PF$_6^-$ as counterion) demonstrated the highest anti-cancer potency with mean IC$_{50}$ values ranging from 2.79-18.6 μM, the lower the IC$_{50}$ values, the higher the anti-cancer potency. By contrast, the cytotoxicity was lower in LO2 normal human hepatocytes. Complexes of Formula (V) and (VI) showed moderate anti-cancer potency with mean IC$_{50}$ values ranging from 6.92-37.2 μM, whereas complex (VIII) possessed the lowest anti-cancer potency with mean IC$_{50}$ values ranged from 10.4-82.8 μM. The cobalt-polypyridyl complexes in different oxidation states (or in different spin states) with the same substituents on the bipyridine ligand showed similar cytotoxicity on the cancer cells. Although the Co$^{2+}$ and Co$^{3+}$ complexes are considered as inert d$^5$ and lable d$^6$ species, respectively, for bioreductive activation as redox-activated prodrugs through ligand modification, there is no direct relationship in the nature of spin state on the cytotoxic effect. Cobalt-polypyridyl complex of Formula (VII) having OCH$_3$ groups generally exhibited higher anti-cancer potency compared to cobalt-polypyridyl complex of Formula (VI) with an un-substituted bipyridine ligand which was less effective compared to cobalt-polypyridyl complex of Formula (IV) with CH$_3$ groups. On the other hand, the larger coordination sphere size and higher lipophilicity may account for the high IC$_{50}$ values of complex (VIII). By scrutinizing their anti-cancer potencies, it is noteworthy that complex (IV) was found to exhibit specific cytotoxic effects towards cancer cells by demonstrating the lowest mean IC$_{50}$ values in various types of cancer cell lines. Results were summarized in Table 1.

TABLE 1

Mean IC$_{50}$ values [μM] of the prepared cobalt-polypyridyl complexes in various cancer cell lines

| complex | (III) | (IV) | (V) | (VI) | (VII) | (VIII) |
| --- | --- | --- | --- | --- | --- | --- |
| HeLa | 10.1 | 11.9 | 24.2 | 35.9 | 12.8 | 21.3 |
| MCF-7 | 15.4 | 6.03 | 15.8 | 10.1 | 10.8 | 37.4 |
| H1299 | 3.43 | 2.84 | 9.4 | 14.9 | 8.71 | 26.7 |
| H1975 | 15.4 | 8.84 | 17.0 | 21.0 | 9.31 | 24.2 |
| A549 | 9.45 | 7.86 | 26.3 | 37.2 | 18.6 | 82.8 |
| LLC-1 | 2.79 | 3.39 | 17.2 | 29.2 | 8.71 | 10.4 |
| HepG2 | 7.39 | 5.44 | 13.3 | 22.7 | 15.4 | 26.0 |
| Hep 3B | 4.06 | 3.7 | 6.92 | 13.8 | 5.33 | 54.1 |
| LO2 | 13.5 | 13.2 | 33.6 | 43.7 | 20.6 | 40.2 |

Example 3

Collateral Sensitivity in Taxol-Resistant and p53-Deficient Cancer Cells

All prepared cobalt-polypyridyl complexes were dissolved in DMSO at a final concentration of 50 mmol/L and stored at −20° C. before use. Cytotoxicity was assessed by using the 3-(4,5-dimethylthiazol-2-yl)-2,5-diphenyltetrazolium bromide (MTT) (5.0 mg/ml) assay as previously described (Wong, V. K. et al., Cell Death Dis, 2013, 4, e720). Briefly, $4\times10^3$ cells per well were seeded in 96-well plates before drug treatments. After overnight culture, the cells were then exposed to different concentrations of selected compounds (0.039-100 μmol/L) for 72 h. Cells without drug treatment were used as control. Subsequently, MTT (10 μL) solution was added to each well and incubated at 37° C. for 4 h followed by the addition of 100 μL solubilization buffer (10% SDS in 0.01 mol/L HCl) and overnight incubation. $A_{570}$ nm was then determined in each well on the next day. The percentage of cell viability was calculated using the following formula: Cell viability (%)=$A_{treated}/A_{control}\times100$. Data were obtained from three independent experiments.

As shown in Table 2, nearly all cobalt-polypyridyl complexes displayed lower mean $IC_{50}$ values in taxol-resistant cancers which are P-glycoprotein-dependent among others when compared to their taxol-sensitive cells in MCF-7, HCT8 and A549 cancer cells, with a Resistant Factor ($IC_{50}$ values of taxol-resistant cells over the $IC_{50}$ values of taxol-sensitive cells) below 0.8, suggesting that these cobalt-polypyridyl complexes exhibit collateral sensitivity towards the taxol-resistant cancers. Compared with the cytotoxicity effect to the drug-sensitive cancer, the cobalt-polypyridyl complexes of Formula (III), (IV) and (VII) (with $PF_6^-$ as counterion) demonstrated the most potent cytotoxic effect towards these taxol-resistant cancers. In addition, cisplatin-sensitive and -resistant pair of cancer cells including A2780 ovarian cancer, SGC-7901 gastric cancer, OV2008 and C13 cervical cancer were further adopted to examine the collateral sensitivity of the cobalt-polypyridyl complexes as presented in Table 3.

Only the cobalt-polypyridyl complexes of Formula (III), (IV) and (VII) (with $PF_6^-$ as counterion) were found to display collateral sensitivity in p53-deficient colon cancer with a Resistant Factor ranging from 0.52 to 0.59 as presented in Table 4, whereas the cobalt-polypyridyl complexes of Formula (III), and (IV) demonstrated the most potent and lowest $IC_{50}$ values in p53-deficient colon cancer.

TABLE 2

Collateral sensitivity of the prepared cobalt-polypyridyl complexes in taxol-resistant cancer cells

| complex | Cancer Types | $IC_{50}$ value, μM Taxol-sensitive cancer | $IC_{50}$ value, μM Taxol-resistant cancer | Resistant Factor |
|---|---|---|---|---|
| (III) | MCF-7 | 4.62 | 2.51 | 0.54 |
|  | HCT8 | 3.13 | 1.16 | 0.37 |
|  | A549 | 9.59 | 2.37 | 0.25 |
| (IV) | MCF-7 | 4 | 2.71 | 0.68 |
|  | HCT8 | 3.39 | 1.22 | 0.36 |
|  | A549 | 11.5 | 2.85 | 0.25 |
| (V) | MCF-7 | 13.4 | 16.8 | 1.25 |
|  | HCT8 | 11.4 | 7.78 | 0.68 |
|  | A549 | 29.9 | 7.85 | 0.26 |
| (VI) | MCF-7 | 8.02 | 5.01 | 0.62 |
|  | HCT8 | 18.5 | 10.2 | 0.55 |
|  | A549 | 51.7 | 11.1 | 0.21 |
| (VII) | MCF-7 | 9.45 | 6.28 | 0.66 |
|  | HCT8 | 4.3 | 1.04 | 0.24 |
|  | A549 | 15 | 2.85 | 0.19 |
| (VIII) | MCF-7 | 28.5 | 11.1 | 0.39 |
|  | HCT8 | 56.4 | 41.1 | 0.73 |

TABLE 3

Collateral sensitivity of the prepared cobalt-polypyridyl complexes in cisplatin-resistant cancer cells

|  | Cancer Types | $IC_{50}$ value, μM cisplatin-sensitive cancer | $IC_{50}$ value, μM cisplatin-resistant cancer | Resistant Factor |
|---|---|---|---|---|
| (III) | A2780 | 11.9 | 11.2 | 0.94 |
|  | SGC-7901 | 11.7 | 17.6 | 1.50 |
|  | OV2008 | 7.06 | — | 2.21 |
|  | OV2008/C13 | — | 15.6 |  |
| (IV) | A2780 | 12.3 | 10.7 | 0.87 |
|  | SGC-7901 | 11.1 | 12.6 | 1.14 |
|  | OV2008 | 7.62 | — | 1.0 |
|  | OV2008/C13 | — | 7.59 |  |
| (V) | A2780 | 28.8 | 31.6 | 1.10 |
|  | SGC-7901 | 29.9 | 29.9 | 1.00 |
|  | OV2008 | 18.9 | — | 0.79 |
|  | OV2008/C13 | — | 14.9 |  |
| (VI) | A2780 | 55 | 54.1 | 0.98 |
|  | SGC-7901 | 41.1 | 41.7 | 1.01 |
|  | OV2008 | 42.5 | — | 0.88 |
|  | OV2008/C13 | — | 37.4 |  |
| (VII) | A2780 | 24 | 27 | 1.13 |
|  | SGC-7901 | 21.6 | 20.7 | 0.96 |
|  | OV2008 | 14 | — | 1.45 |
|  | OV2008/C13 | — | 20.3 |  |
| (VIII) | A2780 | 30.2 | 29.1 | 0.96 |
|  | SGC-7901 | 36.3 | 35.9 | 0.99 |
|  | OV2008 | 49.4 | — | 1.87 |

TABLE 4

Collateral sensitivity of the prepared cobalt-polypyridyl complexes in p53 mutant colon cancer cells ($IC_{50}$ values)

|  | HCT116 p53$^{+/+}$ | HCT116 p53$^{-/-}$ | Resistant Factor |
|---|---|---|---|
| (III) | 17.1 | 8.89 | 0.52 |
| (IV) | 15.4 | 9.07 | 0.59 |
| (V) | 34.3 | 29.1 | 0.85 |
| (VI) | 45.1 | 45 | 1.00 |
| (VII) | 77.8 | 41.3 | 0.53 |

Example 4

Inhibition of Cancer Cell Growth Via Autophagy Induction, Cell Cycle Arrest and Cell Invasion Inhibition Endogenous Autophagy Detection The detection of endogenous LC3 was conducted using immunofluorescence staining method as described below. HeLa cancer cells treated with the cobalt-polypyridyl complex of Formula (IV) (with $PF_6^-$ as counterion) on cover slips were fixed with 4% paraformaldehyde (Sigma) for 20 min at room temperature and then rinsed with PBS. Coverslips were immersed in methanol at room temperature for 2 min. After washing with PBS, the cells were then incubated with anti-LC3 (1:200) in TBST (100 mM TrisHCl, pH 7.5, 150 mM NaCl, 0.05% Tween 20 and 5% BSA) overnight at 4° C. After washing with PBS, the cells were incubated with anti-mouse secondary antibody (TRITC) (1:200) in TBST containing 5% BSA at 37° C. for 1 h in the dark. The coverslips were then mounted with FluorSave™ mounting media (Calbiochem, San Diego, Calif., USA) for fluorescence imaging and localization of LC3 autophagosomes were captured under the API Delta Vision Live-cell Imaging System (Applied Precision Inc., GE Healthcare Company, Washington, USA). To quantify autophagy, guidelines of autophagy quantitation were followed (Klionsky, D. J. et al., Autophagy, 2016, 12, 1-222). The percentage of cells with autophagic induction was calculated by the number of the cells with increased formation of punctate LC3 fluorescence dots (≥10 dots/cell) over the total number of immunofluorescence-positive cells in the same field. A minimum of 1000 cells from randomly selected fields were scored.

Protein Extraction and Western Blotting

After drug treatment, adherent and floating cells were lysed with RIPA lysis buffer. Protein concentrations were determined using the Bio-Rad protein assay (Bio-Rad Laboratories, Inc., Hercules, Calif., USA). The cell lysates of samples were subjected to electrophoresis on SDS polyacrylamide gels and transferred to Hybond enhanced chemiluminescence nitrocellulose membranes (Amersham Biosciences, Piscataway, N.J.), which were then blocked with 5% non-fat dry milk protein for 1 h. Membranes were then incubated with the indicated primary antibodies overnight at 4° C. The binding of the antibody was visualized by peroxidase-coupled secondary antibody using the ECL Western Blotting Detection Reagents (Invitrogen, Paisley, Scotland, UK). Band intensities were quantified by using the software ImageJ (NIH, Bethesda, Md., USA).

Cell Culture

All cells were obtained from the American Type Culture Collection (Rockville, Md., USA) unless otherwise specified. Immortalized wild-type and Atg7-deficient mouse embryonic fibroblasts (MEFs) were provided by Professor Masaaki Komatsu (Juntendo University, School of Medicine, Japan). Taxol-resistant types of A549, MCF-7, HCT-8 cancer cells, cisplatin-resistant SGC7901 cancer cells were purchased from KeyGEN BioTECH, China.

Cisplatin-sensitive or -resistant A2780, OV2008 and C13 cancer cells were provided by Prof. Benjamin Tsang (Department of Obstetrics and Gynecology and Department of Cellular and Molecular Medicine, University of Ottawa, Canada). HCT116 p53$^{+/+}$ and p53$^{-/-}$ isogenic human colon cancer cells were provided by Professor Bert Vogelstein (Ludwig Center at Johns Hopkins, Howard Hughes Medical Institute, USA). All media were supplemented with 10% fetal bovine serum and the antibiotics penicillin (50 U/ml) and streptomycin (50 μg/ml; Invitrogen, Paisley, Scotland, UK). All cell cultures were incubated at 37° C. in a 5% humidified $CO_2$ incubator.

Cell Cycle Analysis

For cell cycle analysis, the cells were harvested and washed with ice-cold phosphate-buffered saline (PBS), and then suspended and permeabilized with 70% ethanol for overnight at 4° C. For detecting DNA content and cell cycle, cells were incubated with the freshly prepared propidium iodide (PI) staining buffer for 30 min at room temperature in dark. Fractions of the cells in G1, S, and G2/M phase were analyzed using Modfit software 3.1.

Cell Invasion Assay

The cancer cell invasion assay was performed in a Cell Invasion Chamber, a 24-well tissue culture plate with cell culture inserts that contain an 8 mm pore size polycarbonate membrane over a thin layer of dried ECMatrix™ (CHEMICON).

Figure 1F:
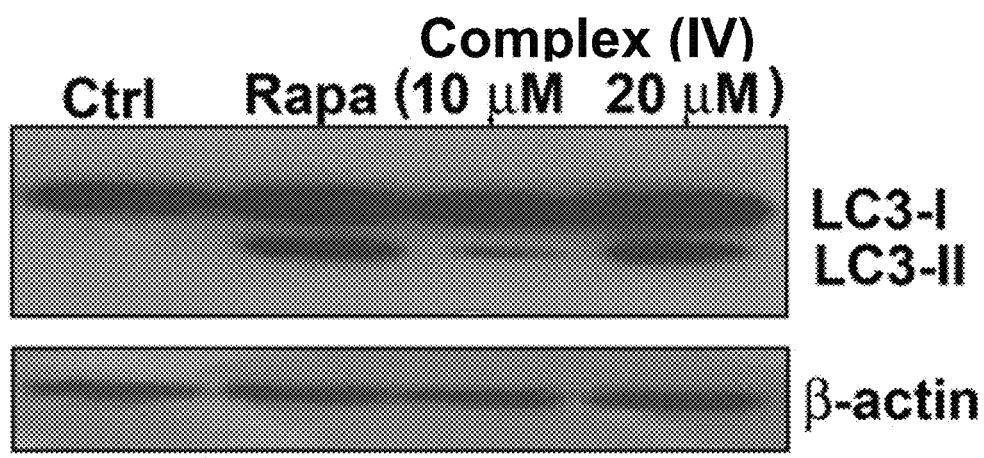
FIG. 1F is a Western Blot showing the expression of LC3-I and LC3-II in the control group and under rapamycin and the cobalt-polypyridyl complex of Formula (IV) with $PF_6^-$ as counterion (10 µM and 20 µM). β-actin was used as control.
Figure 2:
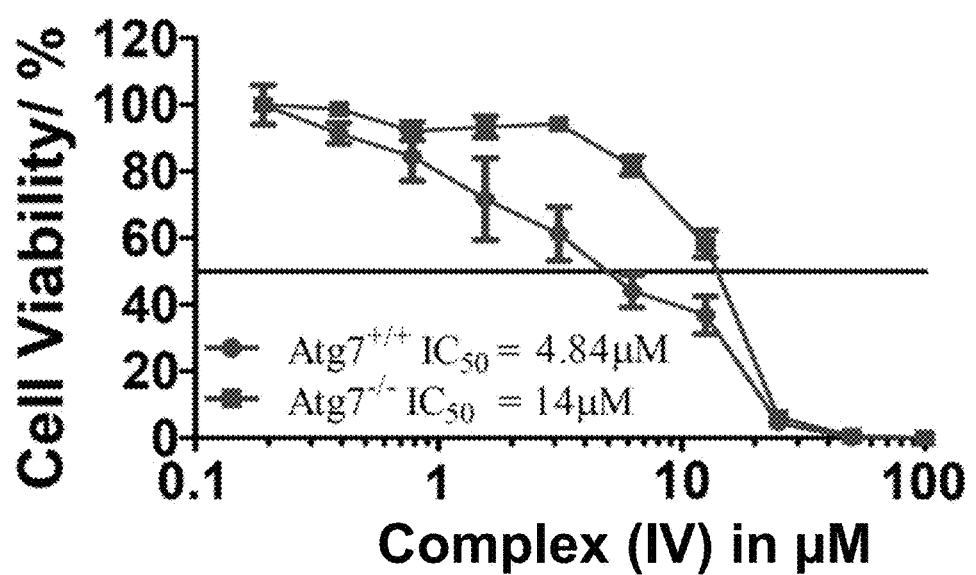
FIG. 2 is a graph showing the cytotoxic effect of the cobalt-polypyridyl complex of Formula (IV) in Atg7 wild-type MEFs and Atg7 deficient MEFs under different concentrations of the cobalt-polypyridyl complex of Formula (IV) with $PF_6^-$ as counterion.
Figure 3A:
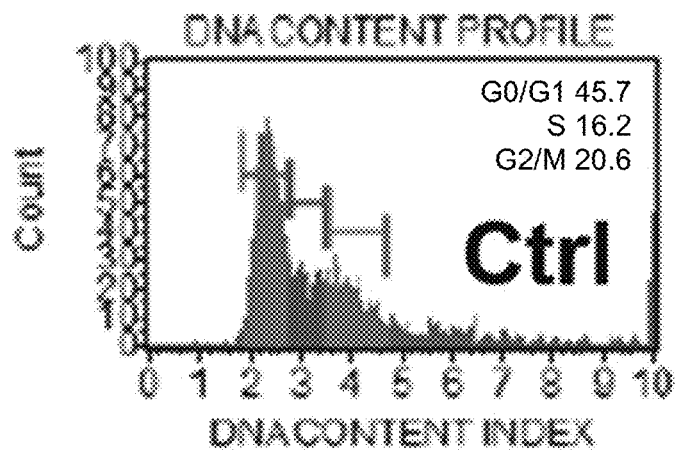
FIGS. 3A, 3B, 3C, 3D and 3E refer to diagrams obtained with flow cytometry analysis and shows the cell cycle progression of HeLa cancer cells treated with the cobalt-polypyridyl complex of Formula (IV) with $PF_6^-$ as counterion.
Figure 3B:
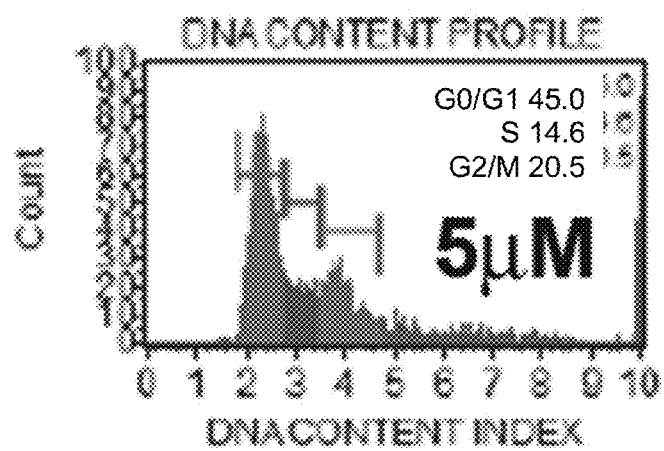
Figure 3C:
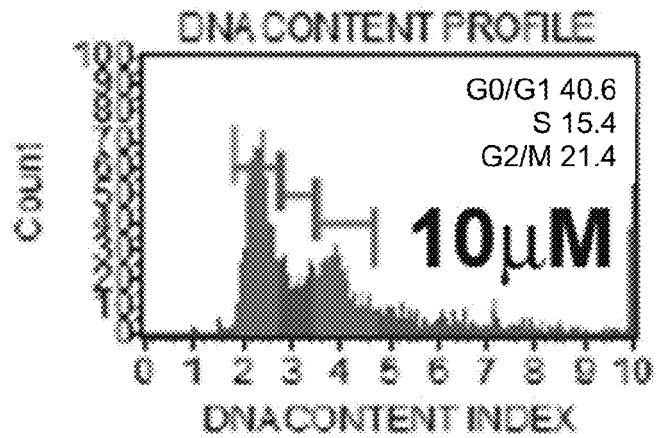
Figure 3D:
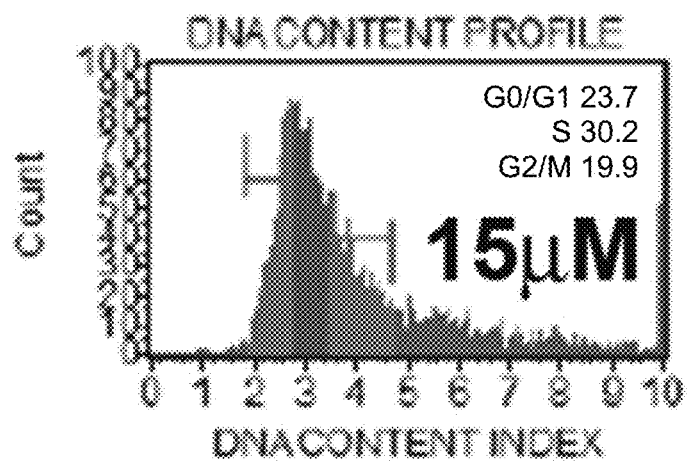
Figure 3E:
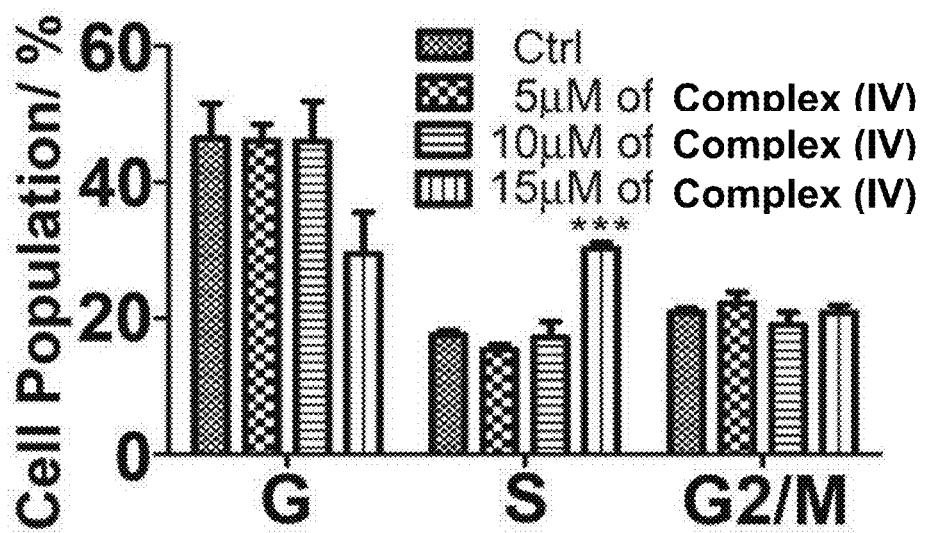

As shown in FIG. 1A to 1D and 1E, the most potent cobalt-polypyridyl complex of Formula (IV) (with $PF_6^-$ as counterion) was found to induce autophagy in dose-dependent manner as indicated by increased percentages of red endogenous LC3-II puncta formation (red TRITC signal), whereas the cells without treatment (Ctrl) showed only slight or no red puncta formation. In addition, the protein conversion from LC3-I to LC3-II is the marker for autophagy induction. Here, is has been demonstrated that the positive control drug, rapamycin (Rapa) increased the LC3-II conversion, whereas the cobalt-polypyridyl complex of Formula (IV) also dose-dependently increased the LC3-II protein conversion (FIG. 1F). In order to further confirm that the cobalt complex-induced autophagy leads to its anticancer effect, the cytotoxic effect of the cobalt-polypyridyl complex of Formula (IV) has been examined in both autophagy-wild type and -deficient cells respectively. Therefore, both autophagy related gene (Atg) 7 wild-type and deficient mouse embryonic fibroblasts (MEFs) (Wong, V. K. et al., Cell Death Dis, 2013, 4, e720) were used in this study. The cobalt-polypyridyl complex of Formula (III) showed much lower $IC_{50}$ value in Atg7 wild-type MEFs (mean $IC_{50}$, 4.84 μM) (FIG. 2), whereas less toxic effect in autophagy deficient cells (Atg7 deficient MEFs, mean $IC_{50}$, 14 μM) was observed. In view of the fact that the cobalt-polypyridyl complex of Formula (IV)-mediated cytotoxicity was markedly abrogated from the failure of autophagy induction in Atg7−/− deficient cells, these findings implicated that the cobalt-polypyridyl complex of Formula (IV)-induced autophagy would ultimately led to autophagic cell death.

To investigate whether the cobalt-polypyridyl complexes could suppress cancer cell growth by arresting cell cycle progression, HeLa cancer cells were treated with different concentrations of the cobalt-polypyridyl complex of Formula (IV) (with $PF_6^-$ as counterion). Apparently, low concentration of the cobalt-polypyridyl complex of Formula (IV) showed negligible effect on cell cycle progression, On the other hand, high concentration of the cobalt-polypyridyl complex of Formula (IV) was found to arrest HeLa cancer cell in S-phase, as determined by the increased percentage of cell population accumulated in S-phase (FIG. 3A to 3E), suggesting that this cobalt complex may affect the DNA replication process in cancer cells.

Figure 4:
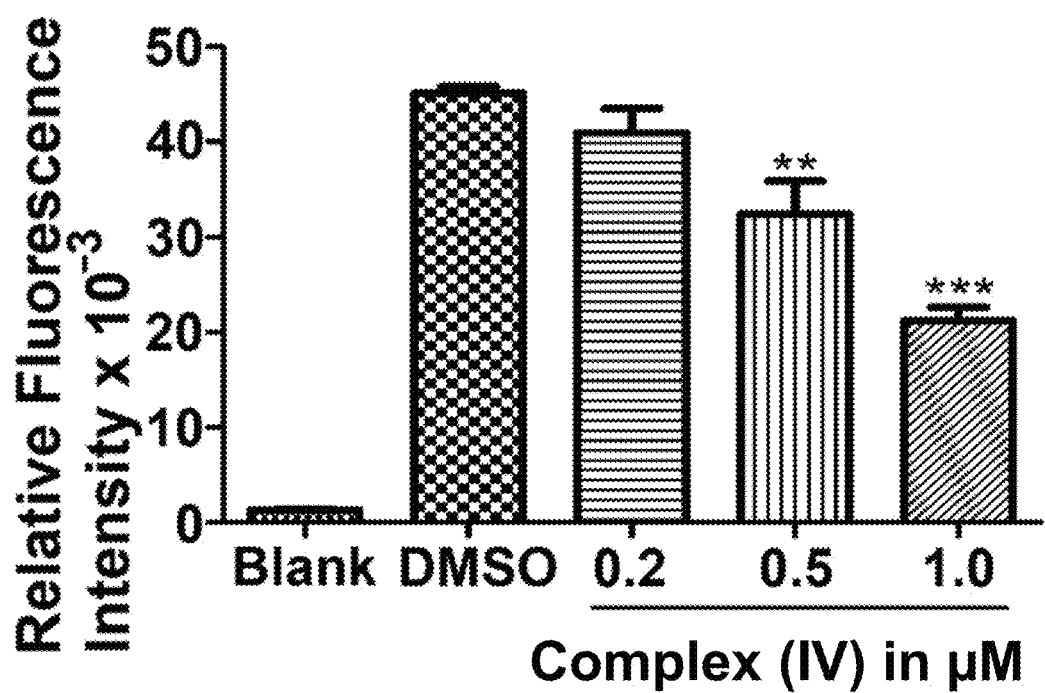
FIG. 4 is a diagram showing the cell invasion ability of cancer cells H1299 upon the treatment with the cobalt-polypyridyl complex of Formula (IV) with $PF_6^-$ as counterion (0.2 µM, 0.5 µM and 1.0 µM) and in control groups.

To determine the inhibitory effect of cobalt-polypyridyl complexes of the present invention in cancer cell invasion, human H1299 lung cancer cells with well-known cell invasion ability were treated with the cobalt-polypyridyl complex of Formula (IV) in its sub-lethal (non-toxic) doses. FIG. 4 shows the invasion assay of cancer cell H1299 upon the treatment with the cobalt-polypyridyl complex of Formula (IV). The H1299 cancer cells treated with DMSO control demonstrated a significant number of invaded cells, as determined by the increased fluorescence intensity. It is noteworthy that the cobalt-polypyridyl complex of Formula (IV) (with $PF_6^-$ as counterion) was found to dose-dependently decrease the cell fluorescence signal, suggesting the cobalt-polypyridyl complex of Formula (IV) could function to suppress cancer cell invasion, and metastasis.

Example 5

Suppression of Cancer Growth in a Mouse Lung Cancer Xenograft Model without Observable Adverse Effects The mice were maintained under specific pathogen-free condition in a 12-h light-dark cycle. Experimental conditions were followed in accordance to the "Institutional AnimalCare and User Committee guidelines" of the Macau University of Science and Technology. Xenograft mouse model was constructed as previously described (Wong, V. K. et al., Oncotarget, 2016, 7, 9907-9924). LLC-1 Lewis lung cancer cells ($1 \times 10^6$ cells) were subcutaneously injected in the right dorsal region of the mice. After tumors grew to about 100 mm³, the mice were randomly divided into 3 groups: 1) the control group, 2) 40 mg/kg cobalt-polypyridyl complex of Formula (IV) group, and 3) 40 mg/kg cobalt-polypyridyl complex of Formula (IV) as chloride, also referenced as (IV)-Cl (water soluble form) group. The cobalt-polypyridyl complex of Formula (IV) was dissolved in 100 µL buffer (PEG400:EtOH:ddH₂O=6:1:3), whereas (IV)-Cl (water soluble form) was dissolved in ddH₂O. The complexes were then intraperitoneal injected in mice every day. The body weight of each mouse was recorded with the tumor volume determined by Vernier caliper using the formula of L×W²×0.52, where L is the longest diameter of tumor and W is the shortest diameter of tumor. Mice with tumor implants were sacrificed after 10 days when the tumor size of vehicle control group reached above 1000 mm³ due to animal ethical issue.

Figure 5A:
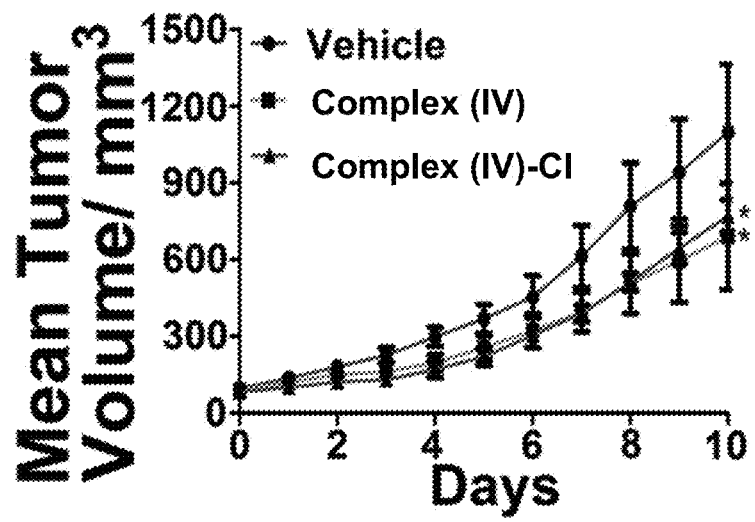
FIG. 5A is a graph showing the mean tumor volume after intraperitoneal (IP) injection of the cobalt-polypyridyl complex of Formula (IV) with $PF_6^-$ as counterion and its water soluble form (complex (IV)-Cl) at 40 mg/kg/day and in a control group demonstrating a significant tumor inhibitory effect of up to 40% (P<0.05) reduction in tumor volume.
Figure 5B:
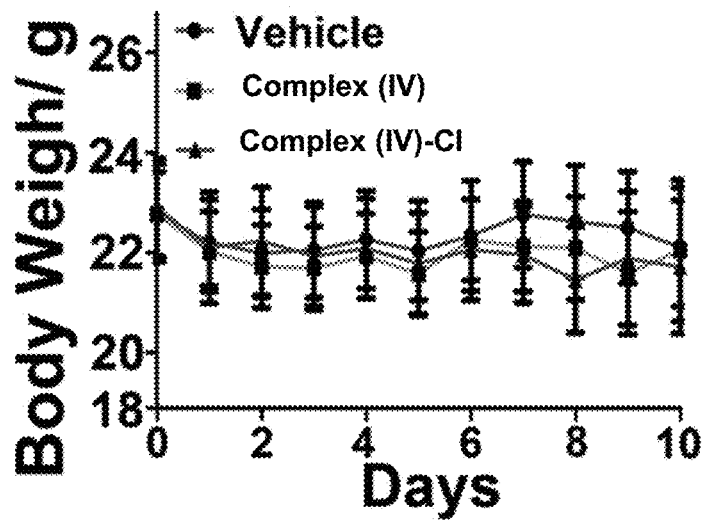
FIG. 5B is a graph showing the reduction in body weight in mice treated with the cobalt-polypyridyl complex of Formula (IV) with $PF_6^-$ as counterion and its water soluble form (complex (IV)-Cl) and in a control group.

The cobalt-polypyridyl complex of Formula (IV) was further assessed in a lung cancer xenograft model in order to investigate its in vivo anti-tumor effect. As shown in FIG. 5A, intraperitoneal (IP) injection of the cobalt-polypyridyl complex of Formula (IV) or its water soluble form (IV)-Cl at 40 mg/kg/day demonstrated significant tumor inhibitory effect of up to 40% (P<0.05) of reduction in tumor volume. Treatment with the cobalt-polypyridyl complex of Formula (IV) or (IV)-Cl showed no significant reduction in body weight (FIG. 5B), suggesting the less or non-toxic nature of the cobalt complex. Collectively, the anti-cancer effect of the cobalt-polypyridyl complex of Formula (IV) not only has been validated in different cancer and multidrug-resistant cancer models, but also in animal system. The results therefore have provided the solid evidence to support that the cobalt complexes represent highly potential anti-cancer drugs.

The invention claimed is:

1. A method for treating a subject suffering from cancer comprising the step of administering an effective amount of a cobalt-polypyridyl complex to a subject, wherein the cobalt-polypyridyl complex comprises structure a of Formula (II):

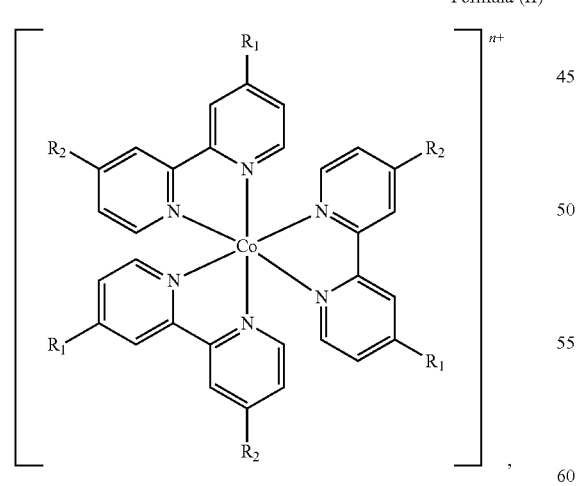

Formula (II)

wherein $R_1$ and $R_2$ are identical and independently selected from hydrogen, a $C_1$-$C_{10}$ alkyl or a $C_1$-$C_{10}$ alkoxy, and n is 2 or 3;
and wherein the cancer is selected from the group consisting of ovarian cancer, cervical cancer, liver cancer, lung cancer, breast cancer, gastric cancer, and colon cancer.

2. The method of claim 1, wherein autophagy of the cancer cells is induced, cell cycle arrest of the cancer cells is induced and/or cell invasion of the cancer cells is inhibited.

3. The method of claim 1, wherein the subject is a human and the cancer is a multidrug-resistant cancer which is at least one of (i) a multidrug-resistant ABC-protein-dependent cancer and/or (ii) a multidrug-resistant apoptosis-deficient cancer.

4. The method of claim 3, wherein the multidrug-resistant cancer is resistant against at least taxol and selected from a multidrug-resistant lung cancer, multidrug-resistant breast cancer, or multidrug-resistant colon cancer.

5. The method of claim 1, wherein $R^1$ and $R^2$ are identical and selected from —H, —CH₃, —C₉H₁₉ or —OCH₃.

6. The method of claim 1, wherein the cobalt-polypyridyl complex comprises a structure selected from Formula (III), Formula (IV) or Formula (VII):

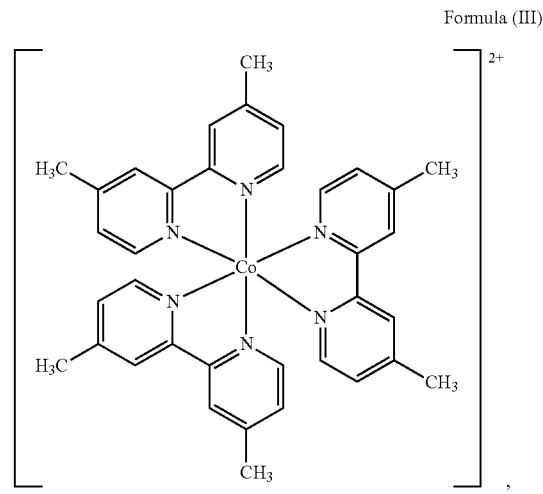

Formula (III)

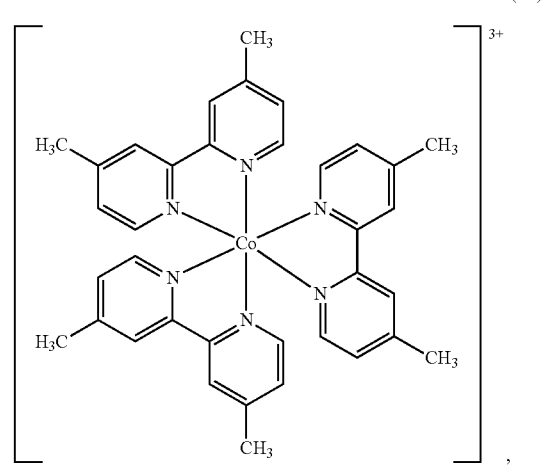

Formula (IV)

or

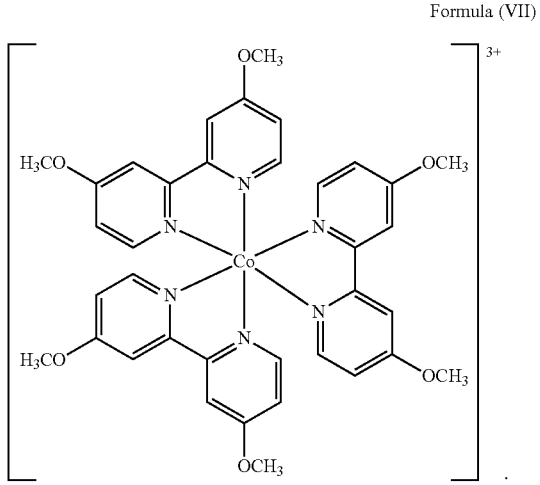

Formula (VII)

7. The method of claim 1, wherein the cobalt-polypyridyl complex is administered in combination with:
   (ii) an effective amount of at least one chemotherapeutic compound, which chemotherapeutic compound is a compound selected from the group consisting of a topoisomerase-II inhibitor, an anthracycline, a coordination complex of platinum, a taxane, a protein kinase inhibitor, a *vinca* alkaloid or derivative thereof, a topoisomerase-I inhibitor and a nucleotide analog or precursor analog;
   (ii) radiotherapy, and/or
   (iii) immunotherapy.

8. A method for suppressing the growth of cancer cells comprising contacting the cancer cells with an effective amount of a cobalt-polypyridyl complex, wherein the cobalt-polypyridyl complex comprises a structure of Formula (II):

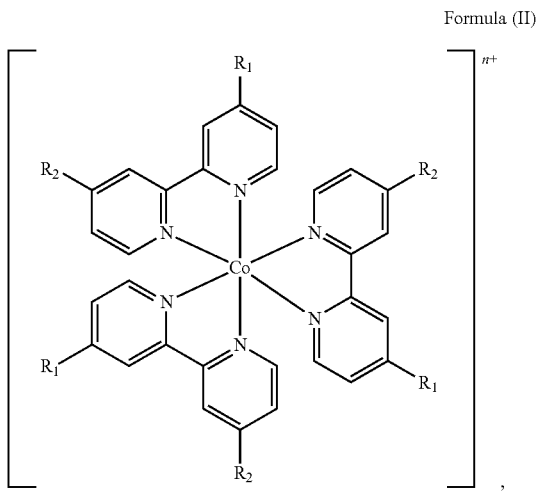

Formula (II)

wherein $R_1$ and $R_2$ are identical and independently selected from hydrogen, a $C_1$-$C_{10}$ alkyl or a $C_1$-$C_{10}$ alkoxy, and n is 2 or 3;
and wherein the cancer cells are from one of an ovarian cancer, a cervical cancer, a liver cancer, a lung cancer, a breast cancer, a gastric cancer and, a colon cancer.

9. The method of claim 8, wherein autophagy of the cancer cells is induced, cell cycle arrest of the cancer cells is induced and/or cell invasion of the cancer cells is inhibited.

10. The method of claim 8, wherein the cancer cells are multidrug-resistant cancer cells.

11. The method of claim 10, wherein the multidrug-resistant cancer cells are at least one of (i) multidrug-resistant P-glycoprotein-dependent cancer cells and/or (ii) multidrug-resistant p53-deficient cancer cells.

12. The method of claim 10, wherein the multidrug-resistant cancer cells are at least resistant against taxol.

13. The method of claim 10, wherein the Resistant Factor of the cobalt-polypyridyl complex towards the multidrug-resistant cancer cells is less than 0.6.

14. The method of claim 8, wherein the $IC_{50}$ of the cobalt-polypyridyl complex against the cancer cells is at most 10 μM with an $IC_{50}$ against non-cancerous being at least 2 times higher.

15. The method of claim 8, wherein the cobalt-polypyridyl complex comprises a structure of Formula (IV):

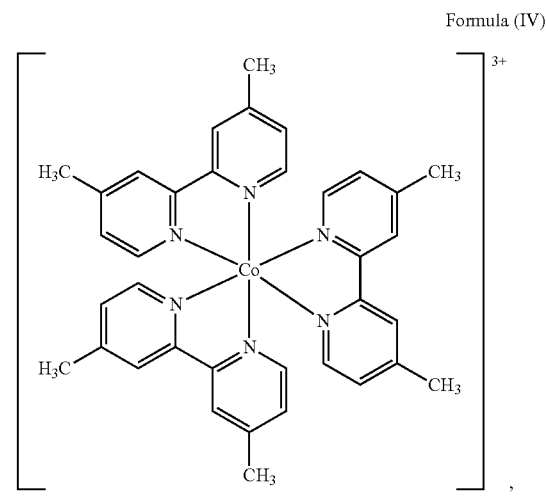

Formula (IV)

and wherein the cancer cells are contacted with of from about 1 μM to about 30 μM of said cobalt-polypyridyl complex.

16. A pharmaceutical composition comprising an effective dose of:
   (i) a cobalt-polypyridyl complex comprising a structure of Formula (II):

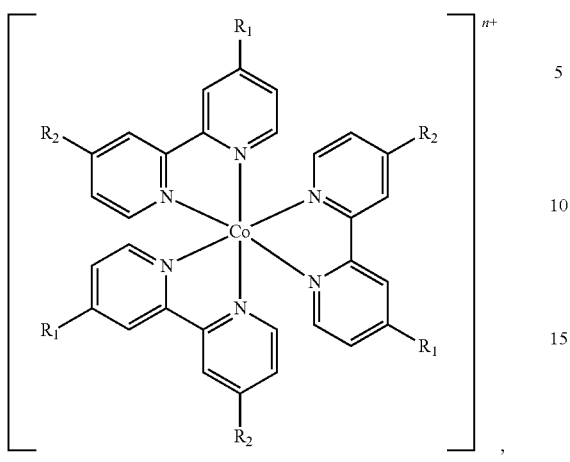

Formula (II)

wherein $R_1$ and $R_2$ are identical and independently selected from hydrogen, a $C_1$-$C_{10}$ alkyl or a $C_1$-$C_{10}$ alkoxy, and n is 2 or 3; and
  (ii) at least one pharmaceutically acceptable excipient selected from a diluent, a filler, a binder, a disintegrant, a lubricant, a coloring agent, a surfactant or a preservative.

17. The pharmaceutical composition of claim 16, wherein the cobalt-polypyridyl complex comprises a structure of Formula (IV):

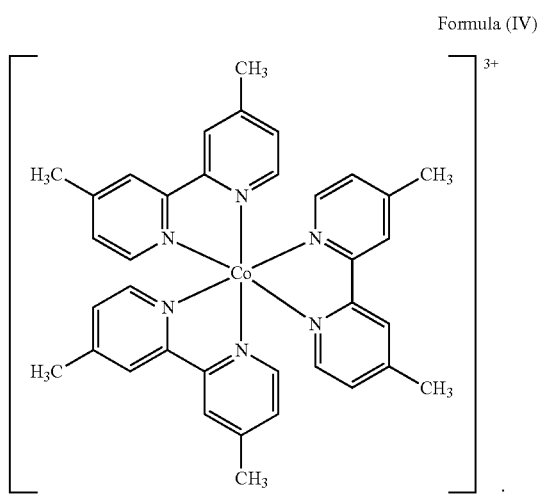

Formula (IV)

* * * * *